United States Patent [19]
Joshi et al.

[11] Patent Number: 6,042,704
[45] Date of Patent: *Mar. 28, 2000

[54] STORAGE-STABLE, FLUID DISPENSING DEVICE USING A HYDROGEN GAS GENERATOR

[75] Inventors: Ashok V. Joshi; John H. Gordon, both of Salt Lake City; John J. McEvoy, Sandy, all of Utah

[73] Assignee: Ceramatec, Inc., Salt Lake City, Utah

[*] Notice: This patent is subject to a terminal disclaimer.

[21] Appl. No.: 09/006,426

[22] Filed: Jan. 13, 1998

Related U.S. Application Data

[63] Continuation of application No. 08/539,998, Oct. 6, 1995, Pat. No. 5,707,499.

[51] Int. Cl.[7] ............................... C25B 9/00; C25C 7/00; C25D 17/00
[52] U.S. Cl. ............................................. 204/265; 204/266
[58] Field of Search .................................... 204/265, 266, 204/228, 292, 293; 222/386.5

[56] References Cited

U.S. PATENT DOCUMENTS

| | | |
|---|---|---|
| 338,770 | 3/1886 | Otto . |
| 1,696,774 | 12/1928 | Martin . |
| 1,916,235 | 7/1933 | Ruben . |
| 2,680,449 | 6/1954 | Toulmin, Jr. . |
| 2,807,215 | 9/1957 | Hawxhurst . |
| 2,924,359 | 2/1960 | Beremand . |
| 2,979,897 | 4/1961 | Studhalter et al. . |
| 2,984,188 | 5/1961 | Tuckey et al. . |
| 3,115,280 | 12/1963 | Battista . |
| 3,425,697 | 2/1969 | Svagerko . |
| 3,430,731 | 3/1969 | Satzinger . |
| 3,602,214 | 8/1971 | London et al. . |
| 3,842,939 | 10/1974 | Satzinger . |
| 3,877,989 | 4/1975 | Waldman et al. . |
| 3,894,538 | 7/1975 | Richter . |
| 3,956,018 | 5/1976 | Kozawa . |
| 4,021,598 | 5/1977 | Naruishi et al. . |

(List continued on next page.)

FOREIGN PATENT DOCUMENTS

| | | |
|---|---|---|
| 961420 | 1/1975 | Canada . |
| 0 414 990 | 3/1991 | European Pat. Off. . |
| 0 768 723 | 4/1997 | European Pat. Off. . |
| 2139771 | 2/1973 | Germany . |
| 61-253764 | 11/1986 | Japan . |
| 62-08450 | 1/1987 | Japan . |
| 62-73565 | 4/1987 | Japan . |
| 62-243252 | 10/1987 | Japan . |
| 182457 | 3/1989 | Japan . |
| 2236973 | 9/1990 | Japan . |

*Primary Examiner*—Kathryn Gorgos
*Assistant Examiner*—Wesley A. Nicolas
*Attorney, Agent, or Firm*—Factor and Shaftal

[57] ABSTRACT

A storage stable fluid delivery device including a gas generator in which moisture (water) is involved in the gas generation reaction in which moisture containment is utilized to prevent or retard water loss as disclosed. The moisture containment may be a moisture impermeable membrane as a permanent part of the device and may be utilized in conjunction with the gas generator when the membrane has high gas permeability for the gas being generated. The fluid delivered by such device is typically a liquid having some particular utility in its environment. The liquid dispensed may be a pharmaceutical or some other liquid having a beneficial or curative effect upon an animal or human patient or it may be a liquid such as an insecticide, fumigant, fragrance or other liquid having a relatively high vapor pressure.

5 Claims, 18 Drawing Sheets

U.S. PATENT DOCUMENTS

| | | |
|---|---|---|
| 4,023,648 | 5/1977 | Orlitzky et al. . |
| 4,038,467 | 7/1977 | Lippold et al. . |
| 4,054,726 | 10/1977 | Sauer et al. . |
| 4,068,049 | 1/1978 | Naruishi et al. . |
| 4,091,186 | 5/1978 | Ott et al. . |
| 4,136,236 | 1/1979 | Ruetschi et al. . |
| 4,139,683 | 2/1979 | Sauer et al. . |
| 4,144,382 | 3/1979 | Takeda et al. . |
| 4,189,526 | 2/1980 | Cretzmeyer et al. . |
| 4,192,914 | 3/1980 | Ruetschi . |
| 4,376,810 | 3/1983 | Takeda et al. . |
| 4,617,242 | 10/1986 | Dopp . |
| 4,671,386 | 6/1987 | Orlitzky . |
| 4,735,876 | 4/1988 | Miura et al. . |
| 4,969,874 | 11/1990 | Michel et al. . |
| 4,971,669 | 11/1990 | Wrede et al. . |
| 5,112,465 | 5/1992 | Danielson . |
| 5,186,805 | 2/1993 | Gross et al. . |
| 5,242,565 | 9/1993 | Winsel . |
| 5,242,763 | 9/1993 | Konishi et al. . |
| 5,279,905 | 1/1994 | Mansfield , Jr. et al. . |
| 5,308,711 | 5/1994 | Passaniti et al. . |
| 5,354,264 | 10/1994 | Bae et al. . |
| 5,378,562 | 1/1995 | Passaniti et al. . |
| 5,398,850 | 3/1995 | Sancoff et al. . |
| 5,398,851 | 3/1995 | Sancoff et al. . |
| 5,423,454 | 6/1995 | Lippman et al. ............... 222/1 |
| 5,427,870 | 6/1995 | Joshi et al. ............... 429/27 |
| 5,451,473 | 9/1995 | Oltman et al. . |
| 5,454,922 | 10/1995 | Joshi et al. ............... 204/265 |
| 5,486,431 | 1/1996 | Tuttle et al. . |
| 5,494,495 | 2/1996 | Tuttle . |
| 5,573,646 | 11/1996 | Saito et al. ............... 204/266 |
| 5,580,674 | 12/1996 | Tuttle et al. . |
| 5,593,552 | 1/1997 | Joshi et al. ............... 204/228 |
| 5,603,157 | 2/1997 | Lake et al. . |
| 5,681,435 | 10/1997 | Joshi et al. ............... 204/266 |
| 5,707,499 | 1/1998 | Joshi et al. ............... 204/228 |
| 5,744,014 | 4/1998 | Gordon et al. ............... 204/266 |

STORAGE-STABLE, FLUID DISPENSING DEVICE USING A HYDROGEN GAS GENERATOR

This is a continuation of U.S. application Ser. No. 08/539,998 filed Oct. 6, 1995, now U.S. Pat. No. 5,707,499.

BACKGROUND OF THE INVENTION

1. Field of the Invention

This invention relates generally to fluid dispensing devices employing gas-generating cells as a propulsion component.

2. State of the Art

Various devices have been utilized as fluid-dispensing apparatus, especially for liquid fluids, where the fluids are dispensed over an extended period of time at a predictable, substantially constant rate.

Battista in U.S. Pat. No. 3,115,280 disclosed a device which can be utilized to dispense fluids by generating $H_2$ and $O_2$ gases by electrochemically decomposing water at electrodes. Fluid contained in a flexible reservoir is dispensed as the generated gases pressurize an adjacent chamber in which the reservoir is contained except for an outlet through which the dispensing fluid leaves the device. The aqueous medium which is decomposed to form $H_2$ and $O_2$ gases surrounds the dispensing liquid reservoir.

Richter in U.S. Pat. No. 3,894,538 disclosed a similar device for dispensing a fluid. In this case, the electrochemically generated gas enters a separate chamber (gas chamber) which shares a flexible diaphragm wall with a liquid containing reservoir. As gas is generated, the liquid is dispensed. Richter suggests several means by which gas may be electrochemically generated including through the use of a cell utilizing an anode consisting of zinc, cadmium, or aluminum.

Orlitzky in U.S. Pat. No. 4,023,648 discloses a similar device which utilizes zinc or magnesium anodes in a cell to electrochemically generate hydrogen gas to pressurize a gas chamber separated from a fluid chamber by a "gas-proof diaphragm." Orlitzky claims that the device is constructed "so that it is almost impossible for any of the generated gas to escape."

Similarly, in U.S. Pat. No. 5,242,565, Winsel discloses a hydrogen generating galvanic cell which utilizes zinc anodes in an alkaline electrolyte to displace a fluid.

Bae et. al. in U.S. Pat. No. 5,354,264 discloses a similar device where water is electrochemically decomposed from an aqueous soaked hydrogel to form hydrogen and oxygen to pressurize a gas chamber with a flexible diaphragm shared by a fluid chamber, or the generated gas enters a chamber of a syringe separated from the liquid by a plunger or cylinder.

The devices described hereinabove are not designed for long shelf life, especially when they are mated to bladder type fluid delivery reservoirs. Moreover, the existing art has ignored the fact that the actual fluid delivery rate is a function of both the rate of gas generation and the rate of transport through the gas chamber walls and seals. This is especially true for slow rate devices.

The fluid dispensing devices described above all generate gas in amounts directly proportional to the electrical current passing through the device circuit; however, it has been discovered that the actual fluid delivery rate is a function of materials of construction which affect the rate of gas transport across the gas chamber walls and seals to and from the ambient air in addition to the rate of gas generation. These fluxes can be very significant when hydrogen is the primary gas generated. Typically the gas chamber outer shell of the devices described above is <0.030 inches thickness, and the flexible diaphragm between the gas and liquid chamber is <0.005 inches thickness. Syringe barrels typically are <0.060 inches thickness. Since there is virtually no hydrogen in air, the gradient for permeation of hydrogen leaving the gas chamber is high. In addition, for plastics which are commonly utilized as materials for such devices, the permeation coefficient for hydrogen is higher than that for air. The ratio of hydrogen to air permeation coefficients at 25° C. ranges from as low as 2.1 for cellophane to 93 for polypropylene. Thus permeation of hydrogen leaving the gas chamber always exceeds the permeation of air entering the chamber, resulting in a net flux of gas leaving the chamber. It has been discovered that the overall rate of liquid dispensed from the type of devices described above is a function of the materials utilized for construction, the area of the surfaces, and the material thicknesses, in addition to the gas generation rate. The effects of permeation are most evident when low pumping rates are desired because the effect of permeation is proportionally higher.

Conversely, many users of such devices are concerned about the presence of hydrogen since the gas can react exothermically in the presence of the oxygen in air if exposed to a spark. Thus, it may be desirable to permit the escape of hydrogen quickly and passively when the useful life of the device has ended.

One of the most important success criteria of fluid delivery devices is having adequate shelf-life; typically shelf life greater than two years is required. The prior art does not address this issue. Shelf life of prior art devices is short because of three issues. First is the loss of moisture from the gas generating cell due to permeation through the gas chamber shell or through the flexible diaphragm. Since most of the reactions which generate hydrogen involve the consumption of water, desiccation of the cells typically will have a negative impact resulting in lower performance or shorter than desirable life. Secondly, if the gas generators are the type which consume a metal, if oxygen is uncontrollably admitted to the cell, the metal will oxidize prematurely, and be spent when the device is to be activated. Third, if the gas generators are the type which consume a metal, hydrogen is generated to some degree prematurely. Corrosion inhibitors may be utilized to significantly reduce this effect; nevertheless, some hydrogen generation will occur if the active metal is in the presence of the aqueous solution, especially if the device is exposed to elevated temperature during storage. This hydrogen must be vented passively, otherwise the device will prematurely pressurize resulting in premature dispensing of the liquid, deformation of the device, or an undesirable burst of fluid delivery when the device is first activated. Thus, another object of this invention is to provide guidelines for selection of materials and design of the device which will be conducive to long shelf life.

Another concern of the users of fluid delivery devices when the device is of the type which electrochemically consume a metal to form hydrogen, is the delay before pumping occurs once the device is activated. This is because any oxygen which has diffused into the headspace between the gas generating cell and the flexible diaphragm must be consumed before hydrogen generation begins. It is also an object of this invention to disclose ways to minimize or avoid this start-up delay.

Another concern of the users of fluid delivery devices when the device is of the type which electrochemically consume a metal to form hydrogen is that typically in the prior art, the metals are amalgamated with mercury to reduce the amount of corrosion while being stored. Ultimate disposal of the device results in environmental problems since mercury is toxic and accumulates in the food chain. Another object of this invention is to disclose ways to avoid the need to amalgamate the electrochemically active metals without sacrificing performance.

Winsel in German Patent 3,602,214 discloses a chemical corrosion technique of generating hydrogen gas from a metal in the presence of an aqueous solution. The technique involves plating a second metal over the corroding metal. Similarly, hydrogen generation from chemical corrosion of a metal for fluid delivery is disclosed in German Patent 2,139,771 and Canadian Patent 961,420. Sancoff has disclosed in U.S. Pat. Nos. 5,398,850 and 5,398,851 storage stable devices utilized for dispensing fluids which are driven by carbon dioxide gas released when a material containing carbonates or bicarbonates is combined with an acid. Sancoff's devices have separate compartments for the reacting constituents to prevent them from reacting during storage, and a means to enable the combining of the active constituents at the time of activation. Such devices utilizing carbonates and bicarbonates have the tendency to not deliver at consistent rates without the utilization of pressure relief valves. The devices present herein are capable of providing nearly constant rate delivery without the added complexity of incorporating a pressure relief valve.

SUMMARY

While the general concept of fluid delivery with hydrogen is not new, this invention relates to novel means of generating the hydrogen by chemical corrosion at predictable rates and include features such as long shelf life, adequate utilization efficiency of the hydrogen with respect to fluid delivery, and subsequent passive bleeding of the hydrogen from the gas chamber so that little hydrogen remains shortly after the dispensing process is completed.

A storage-stable fluid dispensing device utilizing a gas-generator, particularly a $H_2$ generator, has been invented. Fluid-dispensing devices of this type are utilized for various purposes, such as the dispensing of fluid medications, vitamins, hormones, pet foods, fertilizers, aromatic substances, insecticides, insect repellents, fragrances, machinery lubricants, and the like. Whether the devices are utilized in consumer, industrial, or medical applications, shelf-life is important in all cases. Typically, a shelf-life of two years minimum is expected. To satisfy this requirement, several novel embodiments of hydrogen generating devices are disclosed which potentially have shelf-life exceeding two years.

One embodiment includes gas generating cells of the type disclosed in the prior U.S. Pat. Nos. 3,894,538; 4,023,648; 5,354,264; or 5,242,565 which are incorporated herein by way of reference. The cells with metal anodes and hydrogen evolving cathodes may be operated galvanically. That is, they do not require a battery in the circuit to function. However, it is advantageous to incorporate in the circuit a DC power supply such as one or more batteries in series or parallel. This enables the same type of cell to generate hydrogen at a higher rate or enables the usage of a larger resistor in the circuit which provides for more stable delivery rate with respect to time, especially if a power supply or battery of flat discharge curve is utilized. Suitable batteries with flat discharge curves include silver oxide/zinc, mercury oxide/zinc, and zinc/air. An embodiment of this invention is the gas generating embodiment where a gas generator which could be operated galvanically is assisted with a non-gas generating battery to increase level of performance.

In all cases, when the gas generating cells are attached to the gas chamber, an opportunity exists for moisture to permeate through the gas chamber to the atmosphere either directly through the gas chamber wall to the atmosphere or else through the flexible diaphragm into the fluid chamber and through the fluid chamber's exterior walls. Conversely, in very high humidities, the gas generating cell may absorb moisture. In the extreme it is possible for the gas generating cell to absorb enough moisture so that the hydrogen evolving electrode structure becomes flooded to the point that when the device is activated, it will not function properly, or leak.

In general it is undesirable to utilize a shell which is completely impermeable such as a metal shell because of the likelihood of some hydrogen which will be generated as the result of metal anode corrosion while the device is in storage. If this hydrogen does not have a minor path to escape, then the gas chamber pressure rises before activation of the device, resulting either in rupture of the device, in premature pumping of the fluid or a fluid delivery surge when the device is activated. Thus, in general it is desirable to utilize a material which has some hydrogen permeability, or combination of impermeable metal shell with a small area of hydrogen permeable material; however, a very good moisture barrier is required between the gas generator's aqueous constituents and the environment. Otherwise the device will become desiccated or flooded and not perform steadily, if at all, once activated.

Some of best materials in terms of moisture barriers which posses some hydrogen permeability are metallized films such as PET or nylon or other polymer materials with metal coatings in the range of $0.3-1.5 \times 10^{-6}$ inches, also excellent is polychlorotrifluoroethylene (PCTFE or Aclar®), and polychlorotrifluoroethylene co polyethylene (PCTFE/PE or Halar®), also good are polyvinylidene chloride (PVDC or Saran®), high density polyethylene (HDPE), oriented polypropylene (OPP), polytetrafluoroethylene (PTFE or Teflon®), PFA (Hostaflon®), and polytetrafluoroethylene-co-hexafluoropropene (Teflon FEP®). Low density polyethylene (LDPE), linear low density polyethylene (LLDPE), and polyester (PET or Mylar®) can also be utilized to reduce moisture permeation. All of these materials have the advantage over metal foil barriers in that the former posses some hydrogen permeability which would permit the escape of any premature hydrogen generation. These materials, utilized themselves or utilized in combination with other materials as a laminate or coating, may be considered for the moisture barrier.

There are alternatives as where to place the moisture barrier. The gas chamber shell itself may be the barrier if a very low moisture permeability material is selected. A disadvantage of this approach is the generally large area through which moisture permeation may occur. Or an impermeable shell may be utilized which includes a port covered with a low moisture permeable but somewhat hydrogen permeable material. Also, an intermediate moisture barrier between the gas generating electrode or constituents and the gas chamber may be utilized. For example, a moisture barrier may be placed internally or externally against the gas generating device gas exit port(s) or between the gas generating electrode of a gas generating cell and the gas exit port(s). In most locations, the intermediate moisture barrier would be permanent, thus the material selected for the moisture barrier would require enough hydrogen permeability such that hydrogen would permeate through the moisture barrier during operation under a reasonable pressure gradient. If the moisture barrier is external to the gas generator gas exit port(s), the moisture barrier may be applied in a manner such that the effective area during storage is the area of the gas exit port(s), but during operation, under pressure of the hydrogen flow, the effective moisture barrier is a larger diameter as the moisture barrier material bows away from the gas exit port(s). Another possibility, if the moisture barrier is to be external to the gas generation device is to have a releasable moisture barrier using good moisture barrier material with releasable adhesive which provides an excellent moisture barrier during storage but flaps open under the pressure of the initial hydrogen generated, or the material may be weak enough so that the material ruptures under the stress of the initial pressure buildup from the initial hydrogen generated. With this approach the effective moisture barrier area can be very small resulting in excellent containment of moisture, but hydrogen may flow freely into the gas chamber once the moisture barrier has released or ruptured.

When gas generating cells are utilized with corrodible anodes such a zinc, aluminum, or magnesium. The moisture barriers mentioned above also increase the shelf life by impeding oxygen from permeating into the gas generating cells at a high rate. A polymer film with a thin coating of palladium is particularly suited as a moisture barrier material at the gas generation cell because it has low moisture permeability, and a very high ratio of hydrogen to oxygen permeability.

Utilizing a permanent moisture barrier of a material with a high hydrogen to oxygen permeability ratio has another advantage which is not obvious, that is, pumping due to hydrogen generation begins sooner after activation if a moisture barrier is utilized. Typically while stored on the shelf, the head space in the gas chamber between the gas generation cell and the flexible diaphragm will equilibrate with air and contain typically 20.9% oxygen. If the gas generation device is the type where a metal oxidizes such as zinc, aluminum, or magnesium, and if there is no moisture barrier between the gas generating cell and the chamber, then the oxygen in the head space will be consumed by the gas generating cell before appreciable hydrogen will be formed. But if a moisture barrier is present between the gas generating cell and the gas chamber with a high hydrogen to oxygen permeability ratio, then oxygen movement into the gas generating cell is impeded and hydrogen generation begins sooner after the time of activation than would otherwise occur without the moisture barrier. This effect is illustrated in FIG. 14 below. To maximize this effect, if the moisture barrier is metallized with a thin layer of palladium, iron/titanium alloy, nickel or such, then the permeability ratio of hydrogen to oxygen will be extremely high resulting in virtually no delay in the onset of pumping due to the presence of oxygen external to the gas generating device. A thin layer of palladium in particular is nearly transparent to hydrogen but will dramatically reduce the transport of oxygen and moisture. Such a thin layer may be applied to a polymer film such as OPP which has high hydrogen permeability. The palladium may be applied for example by vapor deposition or sputtering to achieve to achieve layer thickness of a few angstroms.

Another feature of this invention which relates to minimization of pumping delay at start-up, is the discovery that certain hydrogen generating cells are extremely ineffective in utilizing oxygen at the cathode, and begin evolving hydrogen, even in the presence of oxygen. Such is the case with non-alkaline cells, particularly if the electrolyte includes ammonium chloride. For example, a galvanic cell constructed like a zinc/air cell but with nickel or ruthenium plated nickel or ruthenium plated nickel plated steel mesh electrodes, zinc anode, and an electrolyte consisting substantially of ammonium chloride, zinc chloride and water, will only have an open circuit potential near 500 mV rather than 1.4 V as is the case of a typical zinc/air cell. Then when a load is placed across the cell so that current may pass though the cell, hydrogen will immediately begin evolving from the former cell, while no hydrogen will evolve from the latter cell until virtually all oxygen is absent from the cathode.

To further the end of maintaining long shelf storage life, another construction involves a device designed in a way that the liquid and solid components of the ultimate gas generators are stored in separate compartments. The isolated constituents are then combined at the time of activation. This approach can be utilized for both electrochemical and chemical type gas generators. For electrochemical type gas generators as described in U.S. Pat. Nos. 3,894,538; 4,023, 648; 5,354,264; or 5,242,565 or such, the design is modified such that the solid active materials are contained in their normal locations, but either water or liquid components such as electrolyte are stored in a moisture tight pouch or compartment with a perforatable member. The pouch can be made of materials with low or no moisture permeability such as low corrosion metals, metallized films of PET, nylon or other metallized polymer materials with metal coatings in the range of $0.3-1.5 \times 10^{-6}$ inches, also excellent is polychlorotrifluoroethylene (PCTFE or Aclar®), and polychlorotrifluoroethylene co polyethylene (PCTFE/PE or Halar®), also good are polyvinylidene chloride (PVDC or Saran®), high density polyethylene (HDPE), oriented polypropylene (OPP), polytetrafluoroethylene (PTFE or Teflon®), PFA (Hostaflon®), and polytetrafluoroethylene-co-hexafluoropropene (Teflon FEP®). Low density polyethylene (LDPE), linear low density polyethylene (LLDPE), and polyester (PET or Mylar®) can also be utilized, or combinations of the above materials with other materials as laminates or coatings. If moisture is not allowed to reached the active metal anode of the gas generator, then the material can be completely impermeable to both moisture and hydrogen, thus metal foils could be utilized for the barrier as long as they themselves did not react with the constituents to form gas prematurely while in storage. At the time of activation, the pouch or compartment wall is perforated by some means such that the liquid constituents flow into the solid constituents, resulting in a mixture that is electrochemically active. With this strategy, premature hydrogen generation is negligible and moisture loss is prevented. In addition, the need to include a gassing inhibitor is eliminated unless very low gas generation rate is required once the device is activated since the constituents are separated until the time when gassing contributes to the fluid delivery. This is a tremendous advantage over Winsel's gas generating cell which required amalgamation to minimize gassing to an acceptable level during storage.

A similar structure may be utilized to separate the liquid and solid components of a hydrogen generating corrosion mixture. Certain active metals when in contact with an acid or alkaline solution oxidize and evolve hydrogen. The rate of hydrogen evolution can be very reproducible and is a function of the type of corroding metal such as zinc, iron, aluminum, magnesium, sodium, calcium, manganese, and such, the surface area, and agents which may be added to reduce the rate of reaction. Such agents are commonly utilized in the battery industry to reduce gassing of gas generating cells and are the subjects of numerous patents. The agents may be classified into three categories, alloying agents which serve to make impurities in the active metal to behave less cathodic, coatings which form a passivating oxide layer over the surface of the active metal, or organic inhibitors which are attracted to the active metal surface which becomes coated and inactive. One widely utilized agent for alkaline systems is mercury which is amalgamated with the corrodible metal or mercuric chloride or mercurous chloride which reduce to form amalgamations. Other agents utilized are aluminum sulfate and aluminum potassium sulfate (U.S. Pat. No. 5,034,291), a surfactant $(X)—C_nF_{2n}—(Y)—(CH_2CH_2O)_m—(Z)$ wherein X is —H or —F, Y is —$C_2H_2$—O —$CH_2CH(OH)—CH_2O$—, Z is —$CH_3$, —$PO_3W_2$ or —$SO_3W$ wherein W is an alkali metal, n is 4 to 14 and m is 20 to 100, and the zinc alloy consists of 0.01 to 1 weight % of indium, 0.005 to 0.5% of one or more of lead and bismuth (U.S. Pat. No. 5,128,222), an oxide from the group antimony, bismuth, cadmium, gallium, indium, lead, mercury, thallium, and tin (U.S. Pat. No. 5,232,798), or the agent is at least one element of the group consisting of bismuth, lithium, calcium and aluminum which is free from mercury, lead, cadmium, indium and thallium but includes gallium hydroxide or oxide (U.S. Pat. No. 5,308,374), an oxide or hydroxide of indium, lead, gallium, or bismuth (U.S. Pat. No. 5,376,480), an organic siliconate with 6 or less carbon atoms including methyl siliconate (U.S. Pat. No. 4,617,242), a surface active heteropolar material having polar affinity comprised of an organic phosphate ester having the formula: $[RO(EtO)_n]_x—PO—(OM)_y$, where x+y=3, and M=H, ammonia, amino, or an alkali or alkaline earth metal and R=phenyl or alkyl or alkylaryl or 6–28 carbon atoms (U.S. Pat. No. 4,840,644), the agent is comprised of at least one anionic surfactant and at least one non-ionic surfactant where the anionic surfactant is represented by the formula $R^1(CH_2—CH_2—O)_n—X^1$ wherein $R^1$ is selected from the group consisting of alkyl, aryl alkylaryl and combinations thereof and $X^1$ is selected from an anionic group consisting of an anionic acid group, salt of an anionic acid group, and an anionic phosphate ester group; and n is between about 3 and 40, and where the non-ionic surfactant is represented by the formula $R^2(CH_2—CH_2—O)_n—X^2$ wherein $R^2$ is selected from the group consisting of alkyl, aryl alkylaryl, fluorinated aliphatic groups and combinations thereof; $X^2$ is a non-ionic group and n is between about 3 and 250 (U.S. Pat. No. 5,401,590). Other agents suitable for the battery industry to utilize to reduce gassing in alkaline battery systems may be considered for adjusting the gas generation rate for the fluid delivery application. The disclosure of said patents related to reducing anode corrosion in an alkaline electrolyte are incorporated herein by way of reference. For non alkaline electrolytes, the agents utilized by the battery industry to reduce gassing in Leclanche type cells may be utilized to varying degrees to achieve the desired gas generation rate. Many of the effective agents are disclosed by Morehouse et. al. in "Effect of Inhibitors on the Corrosion of Zinc in Dry-Cell Electrolytes," J. Res. Nat. Bur. Standards, Vol. 40, pp151–161 (1948) These agents include alloying agents, oxidizing agents, and organic coatings including compounds containing the carbonyl group, heterocyclic nitrogen-containing compounds, starches, flours, gluten and organic colloidal compounds. It must be pointed out that Morehouse refers to some agents which are effective at inhibiting hydrogen evolution but which are not suitable for batteries because they have a negative impact on electrochemical performance; however, such agents are still acceptable for a corrosion type gas generator because electrochemical performance is irrelevant. The disclosure of agents related to reducing anode corrosion in a non-alkaline electrolyte is incorporated herein by way of reference.

With respect to gas generation with acidic solutions, Porbaix and Zoubov in *Atlas of Electrochemical Equilibria in Aqueous Solutions*, Cebelcor, Brussels, 1974, p.119 report the relationship between hydrogen gas generation and area for solutions at pH=0 and containing 0.01 mole per liter of lead, iron, or zinc. Thus a particular gas generation rate can be adjusted by adjusting the particle size of the metal powder or pellets. In addition, oxidizing agents such as potassium chromate or dichromate may be utilized to reduce the rate of hydrogen evolution. From an ecological standpoint, it is preferable to avoid the use of amalgamation with mercury and control the rate utilizing other agents. Like the strategy above, the liquid is stored in a moisture tight pouch or compartment, separate from the corrodible metal. The pouch would be made of materials with low or no moisture permeability such as non-corroding metal, PET or nylon or other polymer materials with metal coatings in the range of $0.3–1.5 \times 10^{-6}$ inches, also excellent is polychlorotrifluoroethylene (PCTFE or Aclar®), and polychlorotrifluoroethylene co polyethylene (PCTFE/PE or Halar®), also good are polyvinylidene chloride (PVDC or Saran®), high density polyethylene (HDPE), oriented polypropylene (OPP), polytetrafluoroethylene (PTFE or Teflon®), PFA (Hostaflon®), and polytetrafluoroethylene-co-hexafluoropropene (Teflon FEP®). Low density polyethylene (LDPE), linear low density polyethylene (LLDPE), and polyester (PET or Mylar®) can also be utilized, or combinations of the above materials with other materials as laminates or coatings. At the time of activation, the pouch is perforated by some means such that the liquid constituents flow into the solid constituents, resulting in a mixture that is chemically active. With this structure, premature hydrogen generation is negligible and moisture loss is prevented. Also there are many alternatives which avoid the need to amalgamate the active metal with harmful mercury.

Whether the hydrogen is generated electrochemically or chemically and whether the liquid and solid constituents were initially separated or premixed, the actual fluid delivered from the device will be a function of both the gas generated and the net flux of gases from the gas chamber. In general, the flux of a particular gas constituent across a film or membrane can be calculated using well known equations:

$$J_i = P_i \times (\Delta p_i) A / t$$

where:

$J^i$ is the flux of constituent I across the film or membrane, $P_i$ is the permeation coefficient for constituent I at the relevant temperature, $\Delta p_i$ is the pressure difference of constituent I across the film or membrane, A is the area of the film and, t is the film thickness Hydrogen permeation coefficients typically are 2–100 times higher than oxygen coefficients and are 7–400 times higher than nitrogen coefficients. With respect to the relative concentrations of oxygen and nitrogen in air, hydrogen permeation coefficients are 2–200 times higher than air. Thus, the net flux of gases through the gas chamber shell is outward, resulting in a pumping efficiency of the fluid to be delivered less than 100% with respect to the volume of hydrogen generated. In addition, much of the oxygen which permeates into the gas chamber is consumed by the gas generating cells to form metal oxide since this is a parasitic reaction which will typically occur with the zinc, aluminum, magnesium or such anode in preference to reaction with the electrolyte to form hydrogen. Thus, for a particular volume of liquid to be dispensed from the device, the gas generating cell will require excess capacity to make up for the hydrogen which will permeate outward from the gas chamber and for the oxygen which will permeate into the gas chamber, ultimately reacting with active gas generating cell constituents. From the viewpoint of efficiency, gas chamber shell materials should have low hydrogen and oxygen permeability. The impact of the material is greater as the intended delivery rate is decreased. Polypropylene has one of the highest hydrogen permeation coefficients of the polymers. If polypropylene is selected for the gas chamber shell and the intended delivery rate is on the order of 100 cc/d, then an efficiency of 95% very likely is tolerable, but at 1 cc/d the efficiency for a gas chamber shell of 10 cm$^2$ and 0.015 inch thickness would be only <15%. For a rate of 0.2 cc/d the efficiency would be <3%. Under the same conditions, if the shell were constructed from polyvinylidene chloride (PVDC), then the efficiency would remain above 95% for the same range of dispensing rates. Materials which have low hydrogen permeation coefficients in addition to PVDC include metallized films such as PET, nylon or other metallized polymer materials with metal coatings in the range of $0.3-1.5 \times 10^{-6}$ inches, ethyl vinyl alcohol (EVOH), cellophane, polyacrylonitrile (PAN or Barex®), polyvinylfluoride (PVF or Tedlar®), polyvinylidenefluoride (PVDF or Kynar®), nylon, and PET. Polychlorotrifluoroethylene (PCTFE or Aclar®), polyvinylchloride (PVC) and HDPE also have low hydrogen permeability.

Films with metallized coatings of aluminum have hydrogen permeability low enough to result in high efficiencies, even at low fluid dispensing rates. For example, a gas chamber constructed from material such as unmetallized PET with 10 cm$^2$ area and 0.015 inch thickness would provide relatively high efficiency (>95%) at a delivery rate of 1 cc per day but <50% efficiency if the rate were only 0.04 cc per day; however, even a modest metallized coating (0.0000005 inch) of aluminum would provide a combination which would offer >90% efficiency even at the lower rate or 0.04 cc per day. Thus for low rates, materials must be selected which have the best barrier characteristics or the device must be provided with very large capacity to compensate for the low efficiency. The materials mentioned above may be used in combination with each other or with other materials to attain the desired properties by lamination or coating.

On the other hand, since it is desirable to design the device so that the hydrogen dissipates quickly and passively after it has completed its delivery cycle, materials or combinations of materials may be selected such that the hydrogen permeation is as high as possible but with acceptable efficiency. Another embodiment of this invention is described below were hydrogen is immediately dissipated.

While EVOH has excellent barrier properties at modest humidities, at high humidities or in the presence of moisture, the gas permeability coefficient of EVOH increases 1000 fold and therefore must be avoided for many applications; however, if the liquid to be dispensed is non-aqueous, and if the gas chamber and liquid chamber shells have low moisture permeability, then EVOH serves well as a flexible diaphragm to separate the gas chamber from the liquid chamber. This is especially true because of its flexibility and extremely low gas permeability.

Another consideration is the concentration of hydrogen in the gas chamber. Some users have a concern about utilizing hydrogen as a driving gas and would prefer that the hydrogen concentration be minimized while the device is operating. Minimizing the hydrogen concentration is accomplished by maximizing the nitrogen permeation into the gas chamber. If an intermediate moisture barrier is not utilized, since any oxygen permeating into the gas chamber is consumed to a large degree by the gas generating cell, nitrogen is the only gas which will significantly accumulate in the gas chamber as the device operates other than on hydrogen. The upper limit to the nitrogen concentration which can be attained while the device operates is the concentration of nitrogen in air (assuming that the device operates in air). Assuming that oxygen is consumed by the device, the minimum theoretical limit to hydrogen concentration in the gas chamber while it is operating is 20.9%. The materials with the highest nitrogen permeation coefficients include polybutadiene, ethyl cellulose, FEP, PTFE, PFA, LDPE, and LLDPE.

Another embodiment of the device which provides for immediate dissipation of the hydrogen driving gas is one where a hydrogen gas generator is utilized but where the hydrogen flows directly into the liquid to be dispensed and carries the liquid vapor into the gas phase. This embodiment requires that the liquid to be dispensed has a significant vapor pressure at the dispensing temperature. The hydrogen flows through the liquid, becoming somewhat saturated with the liquid, then flows through a micro-porous film which is highly permeable to gas or vapor but virtually impervious to liquid. Such a material may be non sintered PTFE. To properly design this device, the liquid chamber should be designed such that the gas must pass through the liquid before passing to the chamber outlet. This type of embodiment is suited for dispensing fluids such as insecticides or fragrances which are to be dispersed into the air. The maximum dispensing efficiency of this embodiment with respect to the gas generated is the ratio of the liquid vapor pressure to the barometric pressure of the environment.

The gas generator disclosed by Orlitzky in U.S. Pat. No. 4,023,648 generates hydrogen electrochemically from a Leclanche type electrolyte which is near neutral pH. In Orlitzky's gas generating cell, the electrolyte substantially is contained together with cathode materials, in particular carbon, and the active anode material substantially only contacts electrolyte at the separator. The gas generator disclosed by Winsel in U.S. Pat. No. 5,242,565 is similar in that hydrogen is electrochemically generated; however, an alkaline electrolyte is utilized which is substantially stored with the anode materials and the hydrogen evolving cathode is substantially only in contact with the electrolyte at the separator.

A disadvantage of Winsel's disclosed gas generating cell is the alkaline electrolyte which is a hazard in the workplace and ultimately in disposal. Also the alkaline electrolyte in Winsel's can slowly absorb carbon dioxide while in storage which can lead to the precipitation of carbonates in the device which may negatively impact performance when the device is activated. Also the active material e.g. zinc in the presence of alkaline electrolyte is more likely to release gas during storage in the absence of gassing inhibitors as discussed above. However, Winsel illustrates that the construction of the gas generating cell may be very similar to a commercial zinc/air button cell battery. Winsel points out that commercial zinc/air button cells can be utilized as hydrogen gas generators when shorted through a load in the absence of oxygen gas. This fact has been well known in the button cell industry for the last 30 years.

The instant invention involves modifications to cells similar to commercial zinc/air batteries which enable them to have long shelf life for the purpose of fluid delivery. This invention also discloses that it is advantageous to utilize the general construction of a zinc/air button cell which is conducive to manufacturing but in which a non-alkaline electrolyte is utilized. Such an electrolyte may be premixed with the anode active material or stored separately, contained in a pouch or compartment in a manner such that the electrolyte mixes with the anode active material when the device is activated. Such electrolyte does not appreciably absorb carbon dioxide, and is not an hazard in the workplace or concern with regard to disposal. Also, unwanted gassing during storage from a combination of a near neutral electrolyte with active metal anode can be readily prevented without resorting to amalgamation with mercury or other heavy metal alloying agents which may be a concern during disposal.

Another embodiment of this invention is one where the active metal anode is incorporated into the cap of the electrochemical gas generating cell. This embodiment, quite unlike constructions utilized in the button cell battery industry, is conducive to manufacturing and provides an advantage over the prior art approaches to hydrogen gas generating cells. The advantage is especially observed in the embodiment where the separator is omitted. As is normal practice in the battery industry, and shown in the figures of Winsel's U.S. Pat. No. 5,242,565, a separator between the electronically conductive cathodic current collector and the electronically conductive anode paste is required. But when the anodic material is part of the cap, and when no electronically conductive material is added to the electrolyte, then the grommet sufficiently isolates the anode from the cathode. Elimination of the separator simplifies the manufacturing of the device and reduces the material requirements.

The advantages of this invention, and how the embodiments are designed for particular applications will be illuminated with the following figures and further description.

BRIEF DESCRIPTION OF THE DRAWINGS

In FIG. 10b the gas generator is coupled with a commercially available battery to increase enable operation at a higher fluid delivery rate or to enable the utilization of a larger resistor in the circuit for more stable delivery.

DETAILED DESCRIPTION OF THE ILLUSTRATED EMBODIMENT

Figure 1A:
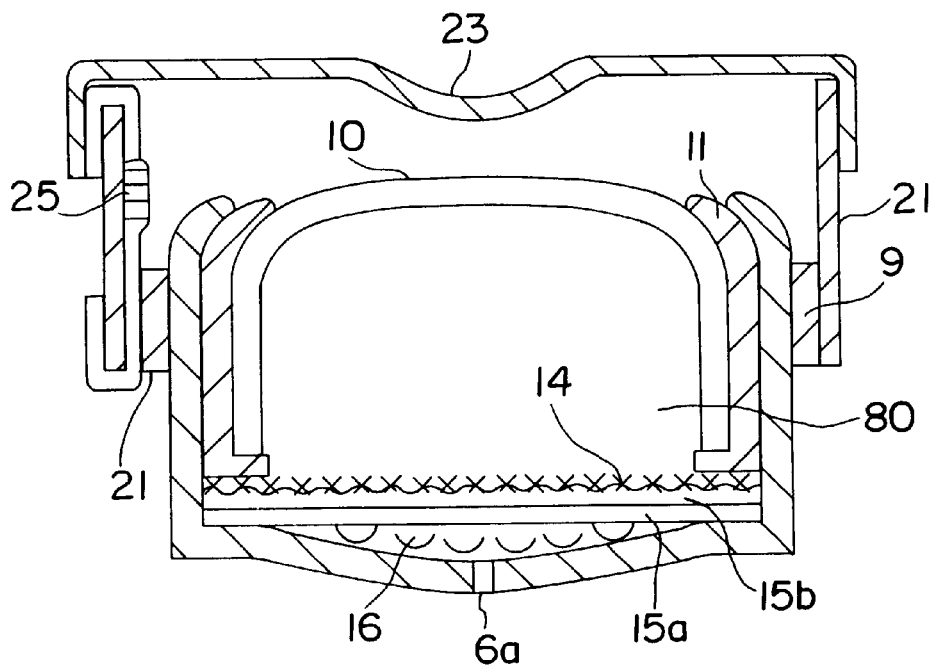
FIGS. 1a–c are cross-sectional views of embodiments of the gas generating portion of the invention which are constructed similar to button cells but where the electroactive metal anode is incorporated into the cap and where ionically conductive separators are not included in the construction.

FIG. 1A is a cross-sectional view of a gas generating device employing an electrochemical cell gas generator, typically generating hydrogen gas. This embodiment is constructed similar to a button cell but with some differences. The embodiment differs from most button cells in that the anode metal is not a powder or gel, thus it is possible to construct the cell without an ionically conductive separator as is typical in battery manufacturing and illustrated by Orilitzky and Winsel in their gas generator designs. The cell, circular in design to simplify manufacturing, is comprised of a cylindrical can 9 which is open at one end and closed except for one or more gas outlet port(s) 6a at the opposite end. The end of said can which has the gas outlet port(s) may be flat or slightly convex. This can may be like the cans typically used in the construction of zinc/air button cell batteries. An optional circular gas diffusion mesh 16 is adjacent to the gas outlet port(s) on the interior of said can. The diffusion mesh diameter is smaller than the inner diameter of said can 9. A seating layer 15a is comprised of either a hydrophobic, micro-porous or gas permeable/liquid impermeable film. Examples of suitable films include microporous or sintered PTFE. An adhesive between sealing layer 15a and the interior perimeter of can 9 is beneficial in improving the effectiveness of the seal. A second hydrophobic, micro-porous layer 15b is intimately contacting a current collector/catalyst layer 14. Said current collector is comprised of a metallic mesh screen. Typically the hydrophobic layer, microporous layer 15b is pressed onto the metallic mesh before die cutting and insertion into said can 9. Said current collector/catalyst layer 14 may be pre-coated by dipping in a slurry of suspended PTFE to facilitate adhesion of said hydrophobic layer, microporous layer 15b. Layers 15a and 15b also may optionally be one single layer. An electronically conductive cell cap 10 comprised of electroactive metal is fitted into an electronically and ionically insulating grommet 11 which together are fitted into said can. The can is crimped around the grommet/cap assembly forming a seal at the perimeter and mechanically pressing the grommet face against said current collector—catalyst layer/hydrophobic layer(s) forming an internal seal. Electronically insulating aqueous electrolyte 80 is contained within the cap. If electrolyte 80 is alkaline such as sodium hydroxide or potassium hydroxide, then nickel or nickel plated steel mesh are examples of suitable materials for said current collector/catalyst layer 14. If electrolyte 80 is non-alkaline such as zinc salt, ammonium salt, lithium salt, magnesium salt, aluminum salt, or combinations thereof, then ruthenium, iridium, platinum, or meshes coated with such are suitable materials for said current collector/catalyst layer 14. It also is desirable to add various corrosion inhibitors to the electrolyte to minimize corrosion of the electroactive metal anode while in storage. For example, if the anode is zinc, and the electrolyte is alkaline, then the addition of zinc oxide, indium oxide, gallium oxide and such are desirable. If the anode is zinc, and the electrolyte is non-alkaline, then the addition of quaternary ammonium salts, gluten containing organics and such are desirable. In addition, gelling agents may be added to the electrolyte to reduce the incidence of leakage.

To activate the gas generator, an activation clip is slid onto the generator. Said activation clip has electronically conductive contact ring 21 which contacts the side wall of the generator can 9. Said contact ring is inserted into one end of an electronically insulating cylinder 22 which has height greater than said contact ring. An electronically conductive contact cup 23 is fitted to the opposite end of said insulating cylinder. The contact cup has a contact indent which contacts said cap of the gas generator at the time of activation. A resistor 25 is placed in electrical communication with both contact ring and contact cup. The activation clip may be already in contact with the can wall when stored, but with the contact indent away from the cap, then at the time of activation said clip is slid so that the circuit is completed.

If the electrolyte 80 is non-alkaline and particularly if the electrolyte substantially includes ammonium salt, as the circuit is completed, hydrogen gas is generated at a rate which is directly proportional to the electrical current flowing through the circuit. As the gas is generated, it flows out of the gas outlet port(s) 6a. The rate of flow of the fluid is affected by the ohmic resistance of said resistor 25. The rate is higher if the resistance is smaller. If the electrolyte is non-alkaline, when the circuit is completed, any oxygen present near the gas outlet port(s) will be consumed by the cell at a rate proportional to the current. Once the oxygen has been consumed, then hydrogen gas generation will begin which is directly proportional to the current.

The active anode metal may be a metal such as zinc, aluminum, or magnesium.

Figure 1B:
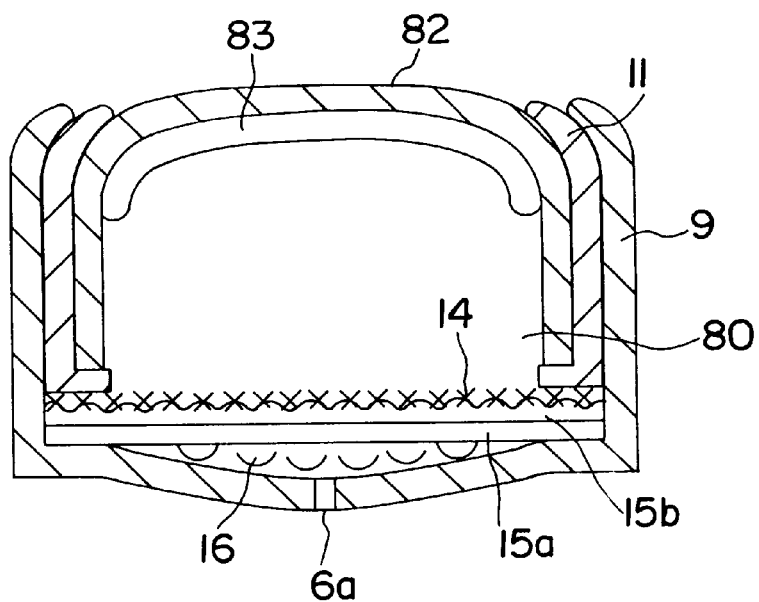

FIG. 1B is a cross-sectional view of a variation of the gas generating device shown in FIG. 1A. Here the cell cap 82 is comprised of an outer shell fabricated from a typical material utilized in the button cell battery industry such as tri-clad nickel/steel/copper laminate, and an insert 83 of the active anode metal is attached to the interior of the cap. The insert may be attached to the cap through various means including welding, adhesives, mechanical, and such. Said cap 82 and insert 83 are in electronic communication with one another.

Figure 1C:
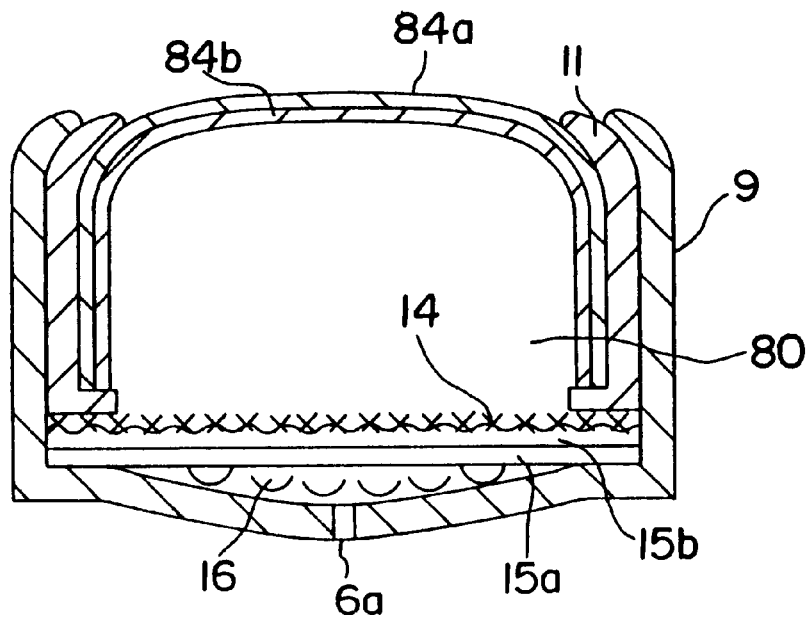

FIG. 1C is a cross-sectional view of a variation of the gas generating device shown in FIG. 1A. Here the cell cap 84a is comprised of an outer shell fabricated from a typical material utilized in the button cell battery industry such as tri-clad nickel/steel/copper laminate but which in addition is clad 84b on the interior with the electroactive metal anode.

Figure 2:
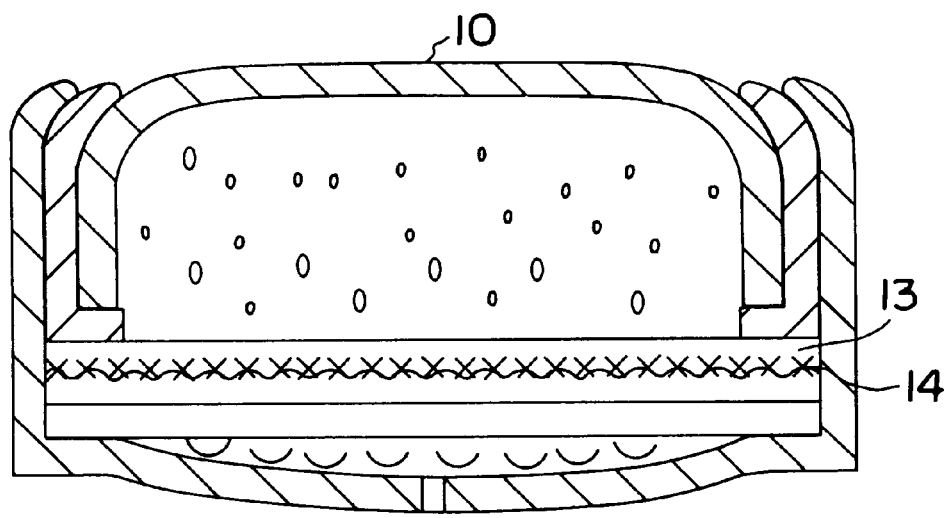
FIG. 2 is a cross-sectional view of an embodiment of the gas generating portion of the invention which is constructed similar to a zinc-air button cell but where an ionically conductive separator is included in the construction.

FIG. 2 is a cross-sectional view of a gas generating device which shares many features of the device shown in FIG. 1; however, in this case a separator is utilized. Cylindrical can 9, gas outlet port(s) 6a, gas diffusion mesh 16, sealing layer 15a and second hydrophobic, micro-porous layer 15b perform the same functions as in FIG. 1A–C. Current collector/catalyst layer 14, in addition to a the metallic meshes described in FIG. 1, may also include catalyst powders or catalyst supported on carbon or graphite powder.

The catalyst may be mixed with a binder such as 5–30% PTFE or mixed with PVA and applied to said metallic meshes. An ionically conductive, electronically insulative, moisture permeable separator 13 is placed adjacent to said current collector/catalyst layer. Several readily available separators are available such as microporous polyolefin, paper, ionomers, or one of the separators utilized for the same purpose in battery manufacturing. If an alkaline electrolyte is utilized, said separator must be conductive to hydroxyl ions and permeable to water. If an alkaline electrolyte is utilized, an example of a suitable catalyst powder for the current collector/catalyst layer includes Raney nickel. If a neutral or acidic electrolyte is utilized, the separator must be conductive to cations. If a neutral or acidic electrolyte is utilized, examples of suitable catalyst powder for the current collector/catalyst layer include supported or unsupported ruthenium, iridium, platinum, or combinations thereof. An electronically conductive cell cap 10 is fitted into an electronically and ionically insulating grommet 11 which together are fitted into said can. Said can is crimped around the grommet/cap assembly forming a seal at the perimeter and mechanically pressing the grommet face against said separator/current collector—catalyst layer/hydrophobic layer forming an internal seal. Electrolyte mix 12 is contained within the cap. The active anode metal of the gas generator is incorporated into said electrolyte mix as a powder or granules. Said electrolyte mix may include a gelling agent. Also, said electrolyte may include an agent to reduce corrosion of the anode during storage.

The gas generating device depicted in FIG. 2 is especially suited for high rates because of the higher surface area of the anode material and the cathode catalyst. If either a powdered anode is utilized or powdered cathode catalyst is utilized, then the separator 13 is required. The devices depicted in FIGS. 1A–C are conducive to manufacturing, have fewer raw materials, and do not have the internal resistances attributable to the separator; thus the devices depicted in FIGS. 1A–C are preferable over a wide range of gas generation rates.

Figure 3:
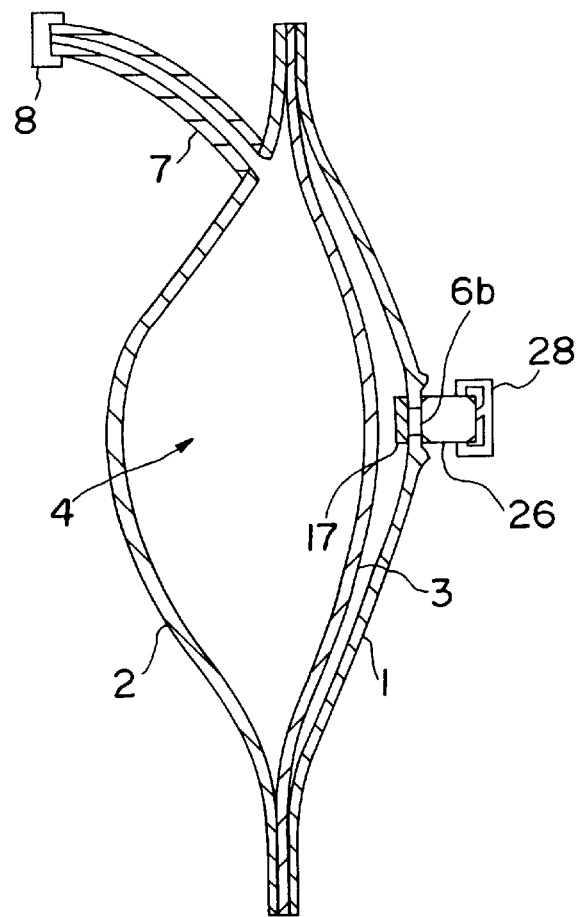
FIG. 3 is a cross-sectional view of an embodiment of the invention where an electrochemical gas generator is integrated with a bladder type fluid container to form an electrochemically controlled fluid delivery.

FIG. 3 is a schematical representation of a gas generating device employing a galvanic cell, gas generator, typically generating hydrogen gas. External gas chamber shell 1 is comprised of a material which has some minimal hydrogen permeability but which is sufficiently low to obtain acceptable efficiency. The shell 1 has very low moisture vapor permeability, a suitable gas chamber shell is somewhat spherical with flanges and is preferably rigid. The liquid chamber shell 2 is also somewhat spherical and is hermetically attached at the perimeter to the perimeter of said gas chamber shell with a flexible diaphragm 3 therebetween. Said liquid shell 2 is comprised of a material which is chemically compatible with the liquid to be dispensed and which has low permeability to the liquid to be dispensed and is preferably rigid. Flexible diaphragm 3 is comprised of a material with low hydrogen permeability, eg. EVOH or metallized polymer films. Initially the gas chamber 5, which is the space between said gas chamber shell 1 and said flexible diaphragm 3 has virtually no volume. Conversely, the liquid chamber 4 which is the space between said liquid chamber shell 2 and flexible diaphragm 3, is filled with the liquid to be dispensed. Liquid chamber 4 has an outlet through which liquid may flow when pressurized. In the embodiment illustrated, a tube 7 and plug 8 are attached to said liquid chamber outlet. Plug 8 is removed at the time of activation.

The gas generation cell may be one of those depicted in FIGS. 1–2. The gas generator shown generally as 26 is sealed to the gas chamber shell 1. A gas inlet port 6b in said gas chamber shell is concentric with gas outlet port 6a in said can. In the embodiment shown in this figure, an intermediate moisture barrier is located between said gas inlet port and gas outlet port. The activation clip is shown generally as 28. To activate the gas generator, an activation clip is slid onto the generator. At the time of activation said clip is slid so that the circuit is completed. As the circuit is completed, hydrogen gas is generated at a rate which is directly proportional to the electrical current flowing through the circuit. As the gas is generated, it flows into the gas chamber and exerts a force against the flexible diaphragm which in turn forces the fluid to flow through the liquid port and outlet tube. The rate of flow of the fluid is affected by the ohmic resistance of said resistor 25. The rate is higher if the resistance is smaller.

FIGS. 4A–E show different locations where an intermediate moisture barrier 17 may be located relative to the gas chamber and gas generator components. If an intermediate moisture barrier is utilized as shown in FIGS. 4A–E, then the gas chamber shell 1 does not require very low moisture permeability properties. The gas generator as a unit is labeled generally as 26 with seal 27 to the gas chamber shell 1.

Figure 4A:
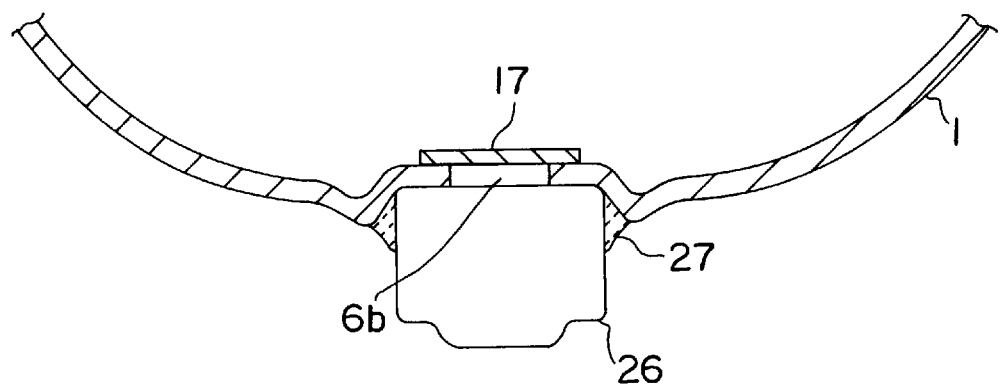
FIGS. 4a–f show different locations where the intermediate moisture barrier may be located relative to the gas chamber and other gas generating cell components.

In FIG. 4A the intermediate moisture barrier 17 is positioned on the interior of the gas chamber shell 1 over the gas inlet port 6b. A barrier in this location may be permanent or releasable.

Figure 4B:
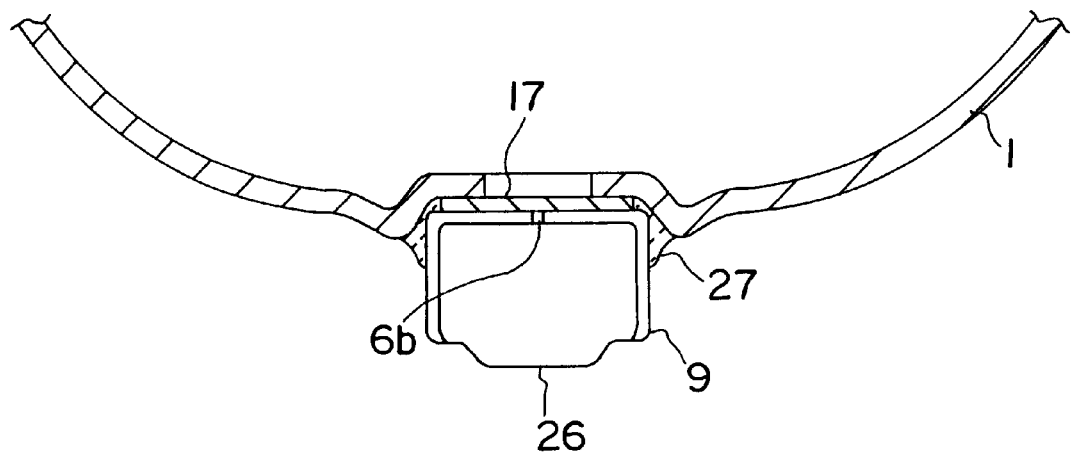

In FIG. 4B the intermediate moisture barrier 17 is positioned between said gas outlet port 6a of the gas generator and gas inlet port 6b of the gas chamber shell. In this position the effective moisture permeation area during storage is the area of said gas outlet port which may be very small.

Figure 4C:
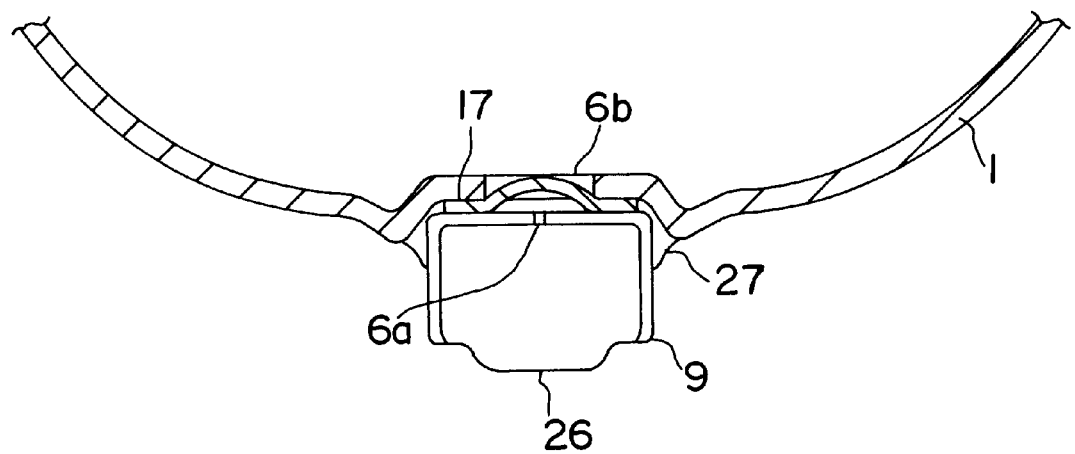

FIG. 4C shows the position of intermediate moisture barrier 17 after the device has been activated and pressure pushes the barrier away from the can 9 such that the effective hydrogen permeation area increases from that of the gas outlet port 6a to that of the larger gas inlet port 6b. This provides a better situation for controlling moisture loss during storage but permitting adequate flow of hydrogen during operation.

Figure 4D:
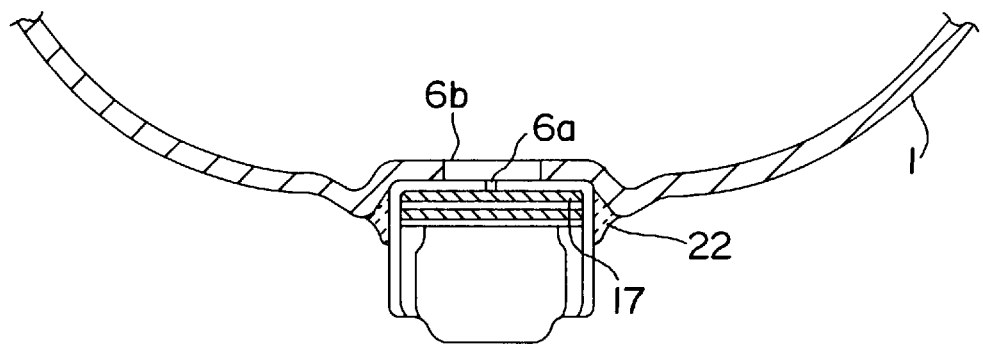

FIG. 4D shows that the intermediate moisture barrier 17 may also be placed inside said gas generator. In this location the effective permeation area before and after activation is that of the gas outlet port.

Figure 4E:
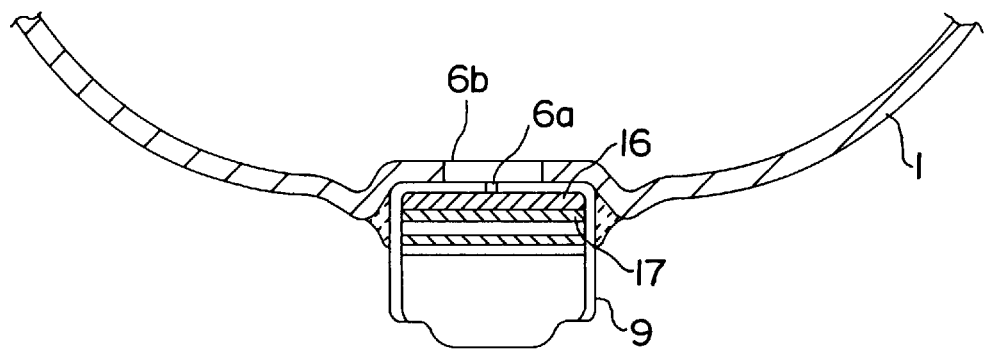

FIG. 4E also shows the intermediate moisture barrier 17 placed inside said gas generator but in this case, diffusion mesh 16 is placed against said can 9 and said intermediate moisture barrier 17 is between said hydrophobic barrier 15 and the mesh 16. In this case the effective permeation area before and after activation is nearly the area of said can.

Figure 4F:
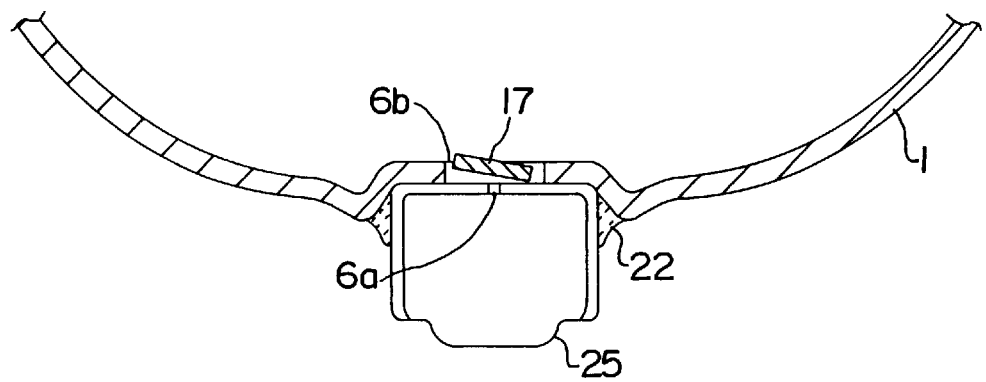

FIG. 4F shows an intermediate moisture barrier which released under the pressure generated from the gas generating device. Thus the benefit of moisture retention during storage was realized without any hindrance to the flow of hydrogen from the gas generating cell during operation.

The moisture barrier useful in the structure illustrated in FIGS. 4A through 4F is one in which water vapor permeation is minimal, preferably approaching zero, while hydrogen gas permeation is sufficiently high such that hydrogen permeates through the barrier substantially as rapidly as it is formed during operation of the gas (hydrogen) generator. The rate of fluid delivery ultimately is controlled by the rate of gas generation. Thus, it is preferred that the moisture vapor barrier has a hydrogen gas permeability which does not retard the rate of hydrogen passage into the gas chamber below the rate of hydrogen generation. Although the gas permeability through the moisture vapor barrier could be used as the rate controller, such a system is not preferred.

Figure 5:
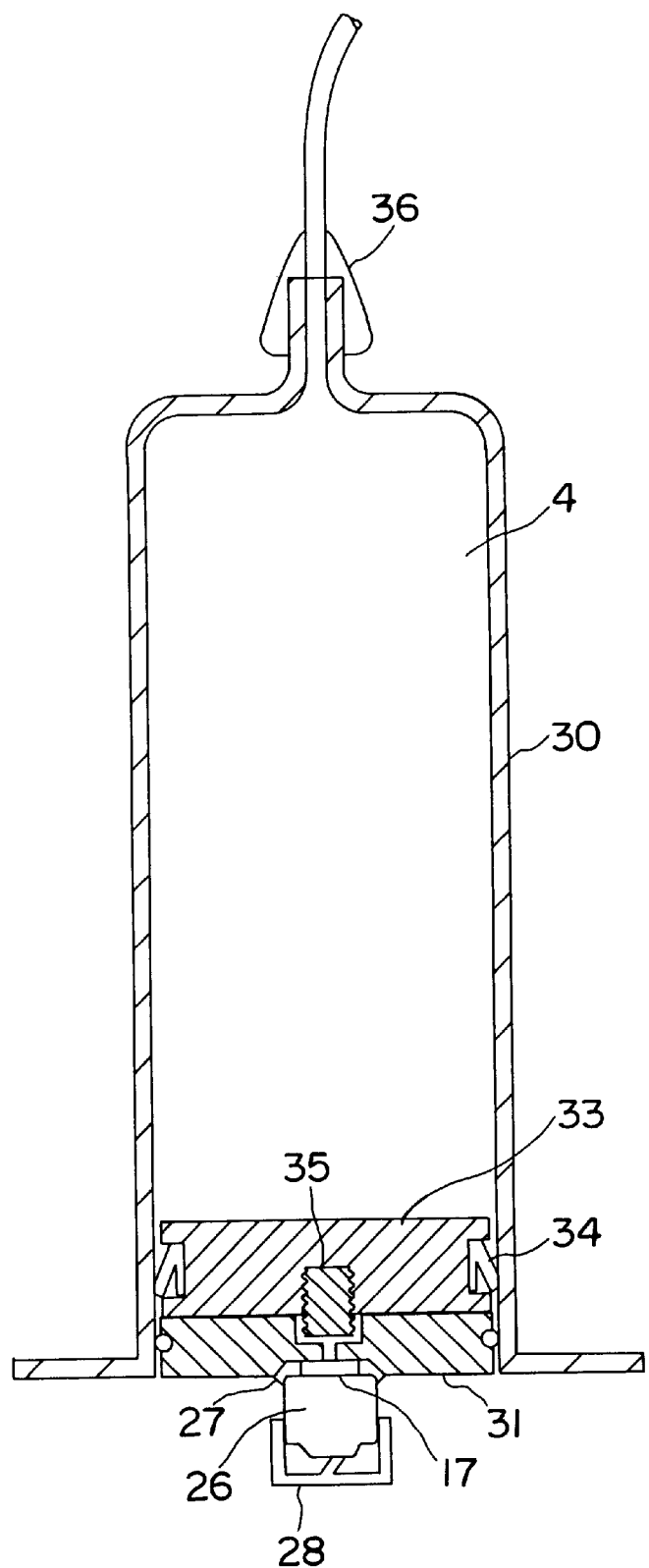
FIG. 5 is a schematical representation of an embodiment of the invention where an electrochemical fluid delivery device with a syringe type fluid container.

FIG. 5 is a schematical representation of an embodiment of the invention where an electrochemical fluid delivery device with a syringe type fluid container. The gas generator as a unit is labeled 26 with seal 27 and activation clip 28. The fluid to be dispensed is contained within liquid chamber 4 which is defined by syringe body 30. The gas generator is attached to an adapter 31 constructed of heavy plastic which is fitted into said syringe body. A piston 33 constructed of heavy plastic or metal is placed into the syringe body. Said piston has one or more seal rings 34 which may be O-rings or U-rings made of elastomer. The U-ring is superior for this application since the rate of fluid delivery is affected less by deviations of the syringe body inner diameter. Polysulfide rubber, nitrile rubber, polyurethane, and FEP rubber, butyl rubber are among the better materials for the seal since they have relatively low hydrogen permeability. Nitrile rubber or Buna N is particularly suitable because it is pliable enough to make a good seal against the syringe body. A threaded insert 35 is provided so that a removable handle (not shown) with female thread can be utilized to drive the piston manually stroke the piston for the purpose of filling the fluid 4 into the syringe. Said adapter 31 is formed in a manner such that said threaded insert 35 of said piston 33 fits into a pocket, minimizing headspace between said adapter and piston. A fluid delivery tip 36 may be connected to a tube set or hypodermic needle. An intermediate moisture barrier in this embodiment was placed between said gas generating cell 26 and adapter gas inlet port 6*b*.

Figure 6:
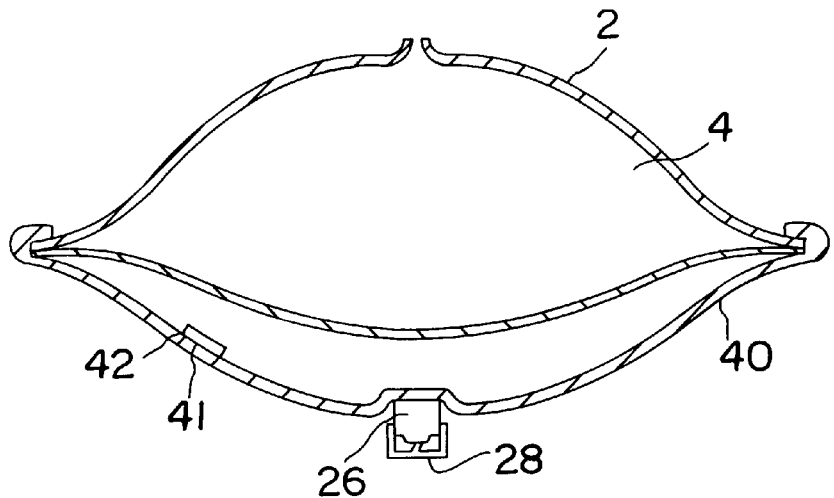
FIG. 6 is a schematical representation of an embodiment of the invention where a fluid delivery device with a metallic bladder type shell with a permeation window.

FIG. 6 is a schematical representation of an embodiment of the invention where the fluid delivery device has a non-permeable gas chamber shell 40 with a permeation window 41. A film 42, which is somewhat permeable to hydrogen to vent inadvertent hydrogen generated during storage but which will inhibit moisture loss, is sealed over the window either on the interior of the shell, as shown, or on the exterior. In this embodiment the gas chamber shell is crimped over the flexible diaphragm and liquid chamber shell in the manner of the beverage can packaging industry.

Figure 7:
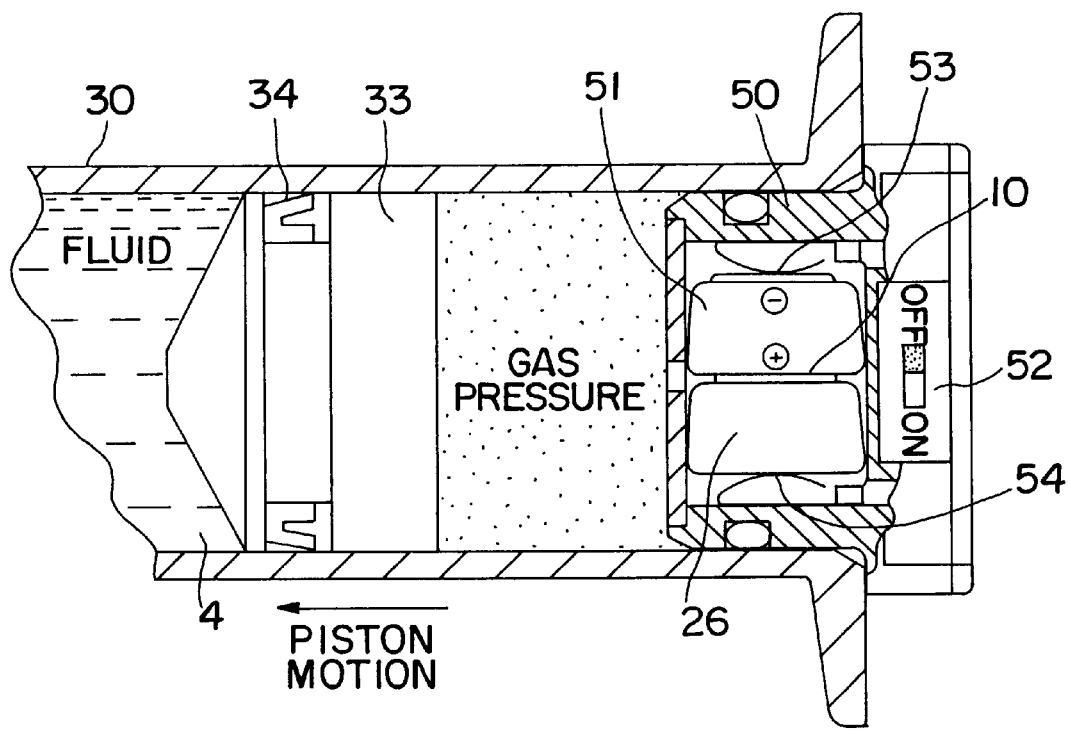
FIG. 7 is a schematical representation of an embodiment of the invention where a battery is utilized to drive the gas generating cell to achieve higher or more stable fluid delivery rates.

FIG. 7 is a schematical representation of an embodiment of the invention where a battery is utilized to drive the gas generating cell to achieve higher or more stable fluid delivery rates. This embodiment is shown to be utilized with a syringe. A housing 50 contains the gas generating cell 26 and a button cell battery 51 which is placed such that the positive battery terminal contacts the cap 10 of said gas generating cell. In this case a commercially available switch 52 is utilized instead of the activation clip. Contacts 53 and 54 are in electrical communication with the switch and a resistor (not shown) to form an electrical circuit with the battery and gas generating cell. In this figure the device is shown with the piston 33 already pushed away from said housing 50 by the generated hydrogen.

Figure 8A:
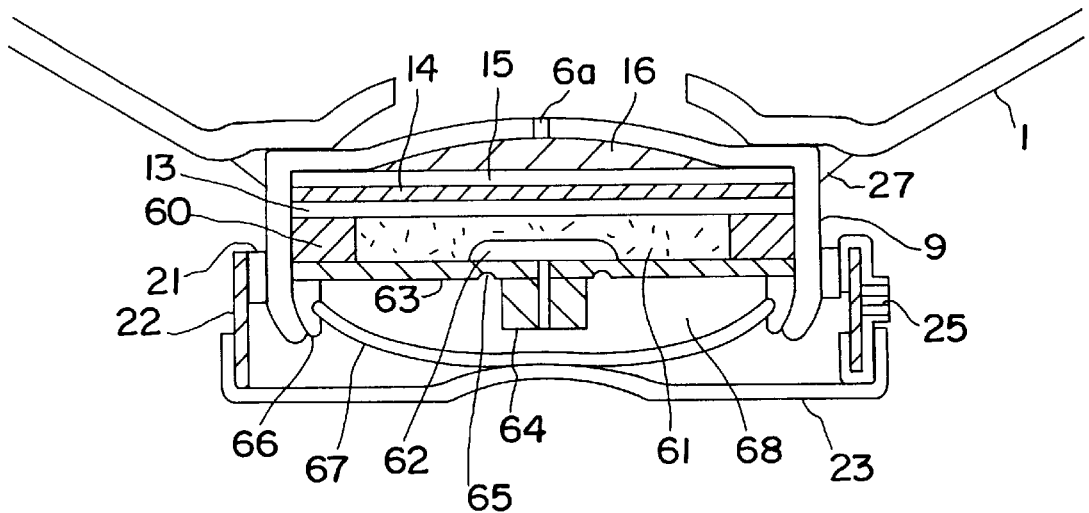
FIG. 8a is a schematical representation of an embodiment of the invention where an electrochemical gas generator has liquid and solid components isolated from each other before activation. The figure also represents, with some modification, the embodiment of the invention which is a corrosion type gas generator.

FIG. 8A is a schematical representation of an embodiment of the invention where an electrochemical gas generator has liquid and solid components isolated from each other before activation. The figure also represents, with some modification, the embodiment of the invention which is a corrosion type gas generator. Construction is similar to the embodiment shown in FIG. 1. Cylindrical can 9, gas outlet port(s) 6*a*, gas diffusion mesh 16, sealing layer 15*a* and second hydrophobic, micro-porous layer 15*b* perform the same functions as in FIG. 2. Current collector/catalyst layer 14, and separator are in the same relative positions and serve the same functions as in FIG. 2. Adjacent to the separator and fitted secure against the can wall is an electronically insulating cylindrical anode grommet 60 which open at both ends. Fitted against said separator and within said anode grommet opening is the active anode metal 61. Said active metal may be a powder pressed into a porous pellet or may be a solid piece but must have access holes such that electrolyte may pass through to the separator. The active anode metal pellet or piece has a void space 62. Divider 63 is formed of a material with low moisture permeability and fits against said anode grommet and is sealed thereto. Breaking structure 64 is either formed with said divider 63 or is a separate part. Electronically conductive flexible cap 67 is fitted into the cap grommet 66. The flexible cap/grommet assembly fits against said divider 63 and is sealed thereto. The can is crimped at the open perimeter over said cap grommet to hold said assembly in place and to compress the internal seal joints. Within said flexible cap is stored the electrolyte 68 with inactive but electronically conductive powder such as graphite or carbon black. The activation clip consisting of contact ring 21, electronically insulating cylinder 22, electronically conductive contact cup 23, contact indent 24, and resistor 25 have the same configuration and serve the same functions as in FIG. 1. In addition, when said activation clip is slid to complete the circuit, said contact indent presses against flexible cap 67 such that said cap presses against said breaking structure 64 which breaks or shears the divider 63 at break zone 65. As said divider is broken, electrolyte and electronically conductive powder flow into void 62 and into the pores within said anode metal 61. As this occurs, the gas generator becomes functional and begins to produce hydrogen galvanically at a rate proportional to the current in the completed circuit. Since the electrolyte is separate from the active metal during storage, there is no inadvertent hydrogen produced during storage, thus the gas chamber shell 1 can be constructed of a completely impermeable material. Also there is negligible moisture loss or gain during storage.

Figure 8B:
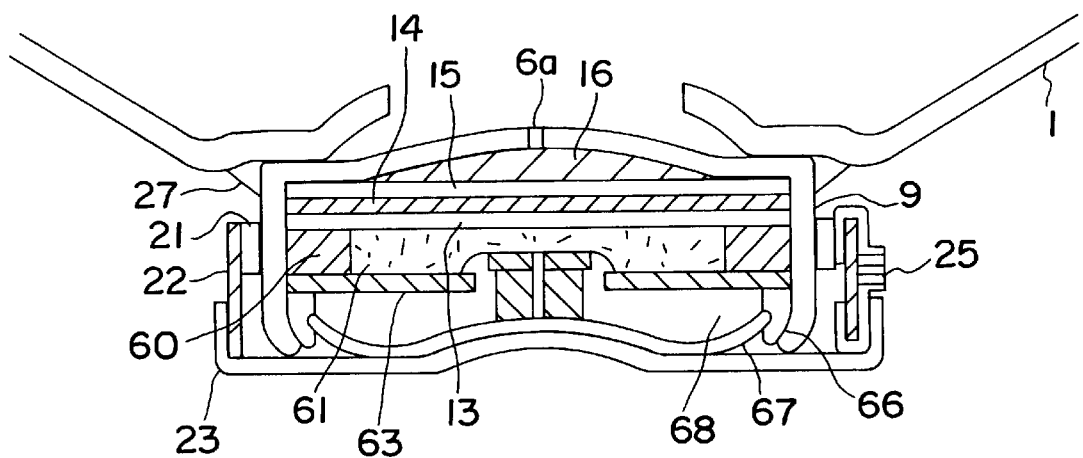
FIG. 8b is a schematical representation of the embodiment shown in FIG. 8a after the device has been activated by breaking the divider.

FIG. 8B shows the gas generating device illustrated in FIG. 8A after it has been activated. The divider 63 has been perforated at break zone 65. Fluid 68 has been forced into contact with active metal 61.

A corrosion type gas generator can be constructed identical to the gas generating cell in FIG. 8A and 8B except said current collector/catalyst layer 14, and separator 13 may be omitted. Also the electronically conductive powder in said electrolyte can be omitted since the active anode metal does not require electrical continuity with said cap. Corrosion reducing agents would either be added to the electrolyte or to the active metal anode to achieve a particular fluid delivery rate. Also said resistor in the activation cap can be omitted. The contact ring 21, insulating cylinder 22, conductive cup 23, and indent 24 can be integrated into a single part formed of a material which is either conductive or insulating. Such a corrosion type gas generating device can also be utilized with a syringe type embodiment.

Figure 9:
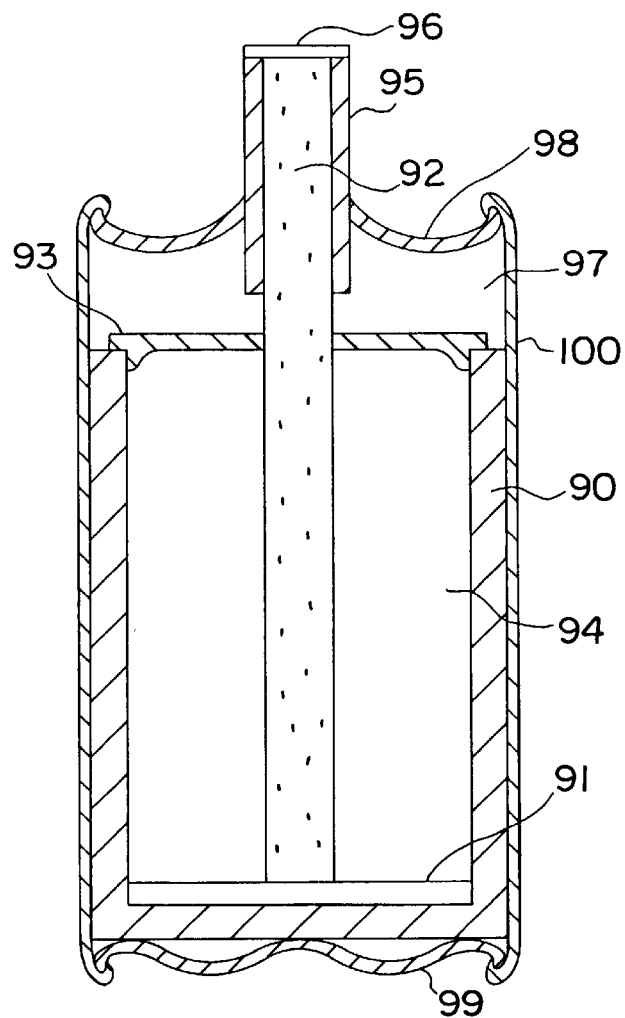
FIG. 9 is a is a cross-sectional view of an embodiment of the gas generating portion of the invention which is constructed similar to a dry cell battery but where depolarizer (manganese oxide or dioxide) and separator are omitted from the construction. In the embodiment shown, a porous carbon or graphite rod serves as the hydrogen evolving cathode and passageway for hydrogen to be directed from the cell into a tubing leading to a fluid containing reservoir.

FIG. 9 is a cross-sectional view of an embodiment of the gas generating portion of the invention which is constructed similar to a dry cell battery but where depolarizer (manganese oxide or dioxide) and separator are omitted from the construction. Cylindrical can 90 is formed of the electroactive metal anode material such as zinc, aluminum or magnesium or alloys thereof. The can is closed at one end. Electronically insulating washer 91 is placed inside the can against the closed end. Electronically porous rod 92 serves as cathode and passageway for the generated hydrogen to exit the cell. Suitable material for the rod would be porous carbon or graphite, particularly carbon or graphite which has some electrocatalytic coating on the surface. Said rod is held concentrically in said can by an insulating washer 93 with a hole through which the rod passes. The can is filled with aqueous electrolyte 94 which may be either alkaline or non-alkaline such as in the cell illustrated in FIG. 1. If the electrolyte is alkaline, examples of suitable electrocatalytic coatings on said rod 92 include nickel or Raney nickel. If the electrolyte is non-alkaline, examples of suitable electrocatalytic coatings on said rod 92 include ruthenium, iridium, platinum or combinations thereof. A gas impermeable, electronically conductive tube 95 such as metal tubing is fitted over the end of said rod 92 so that generated gas can flow axially and not escape radially into the environment. A hydrogen permeable intermediate moisture barrier 96 is placed over the end of said rod 92. The moisture barrier may be permanent, releasable or rupturable so that moisture loss during storage is minimal but hydrogen may pass through the end of the rod at a sufficient rate for the intended application. A sealing material 97 such as pitch is placed adjacent to insulating washer 93 to prevent escape of electrolyte or generated gas. Cathode contact washer 98 electronically communicates with tube 95 and covers sealing material 97. Anode contact washer electronically communicates with the electroactive metal can 90. Said cathode washer and anode washer are crimped to electronically insulating cylindrical jacket 100. The jacket may be comprised of several layers as is common with dry cell batteries. For example, the jacket may include layers of polymer films and paper.

To activate the gas generator, an electrical circuit is completed between the cathode contact washer 98 and anode contact washer 99. The electrical circuit may include a resistor, switch, and optionally a D.C. power source such as a battery. If a D.C. power source is utilized, the negative pole communicates with the cathode contact washer and the positive pole communicates with the anode contact washer. As current is passed, hydrogen forms at the rod 92. As hydrogen is generated, it flows through the rod axially toward the intermediate moisture barrier 96, through which it passes into the gas chamber of a fluid deliver reservoir which is not shown.

Figure 10A:
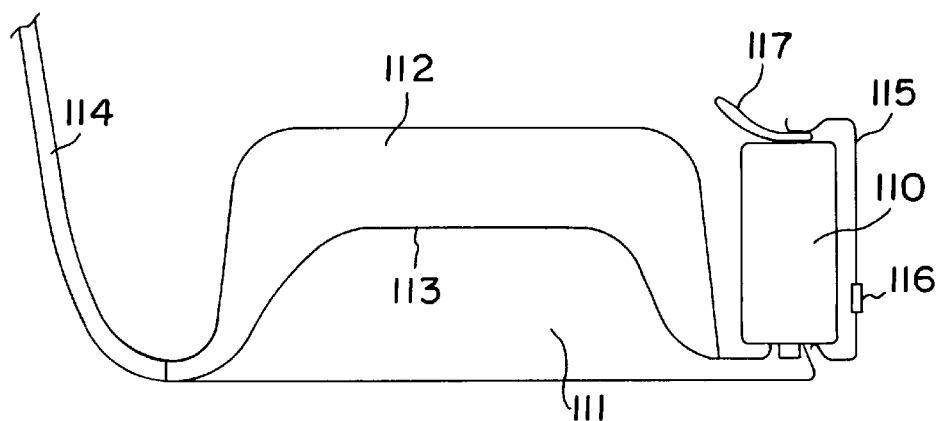
FIGS. 10a and 10b are schematical representations of fluid delivery embodiments utilizing the type of gas generator shown in FIG. 9.

FIG. 10A is a schematical representation of fluid delivery embodiment utilizing the type of gas generator shown in FIG. 9 which is depicted generally as 110. Gas chamber 111 and liquid chamber 112 share a flexible diaphragm 113. Liquid chamber is connected to liquid flow tube 114. Electrical circuit 115 includes resistor 116 and pull tab switch 117. When pull tab switch 117 is removed, the electrical circuit is completed and generated hydrogen enters the gas chamber 111. Flexible diaphragm 113 moves under the increase in pressure to cause fluid to flow from liquid chamber 112 into said liquid flow tube.

Figure 10B:
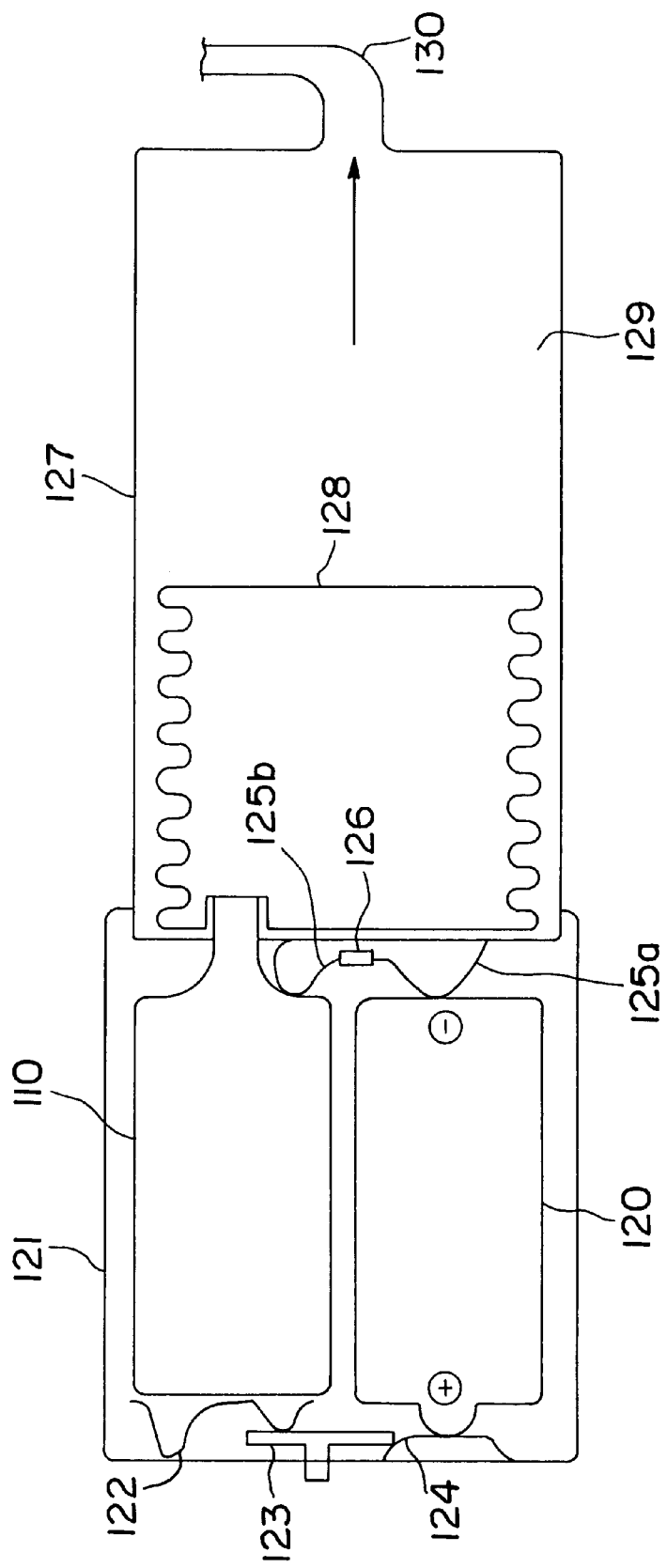

FIGS. 10B is a schematical representation of fluid delivery embodiment utilizing the type of gas generator shown in FIG. 9 which depicted generally as 110. In this embodiment, a commercially available battery is utilized to enable operation at a higher fluid delivery rate or to enable the utilization of a larger resistor in the circuit for more stable delivery. Both gas generator 110 and battery 120 are contained in housing 121. During activation, contact 122 communicates with the anode contact of the gas generator and switch 123. Contact 124 communicates with the positive terminal of battery 120 and said switch. Contact 125a communicates with the negative terminal of said battery 120 and resistor 126. Contact 125b communicates with cathode contact of said gas generator 110 and the resistor. As current passes through the circuit, gas flows into bellows 128. As bellows expand, liquid 129 is pushed from liquid chamber 127 into flow tube 130.

Figure 11:
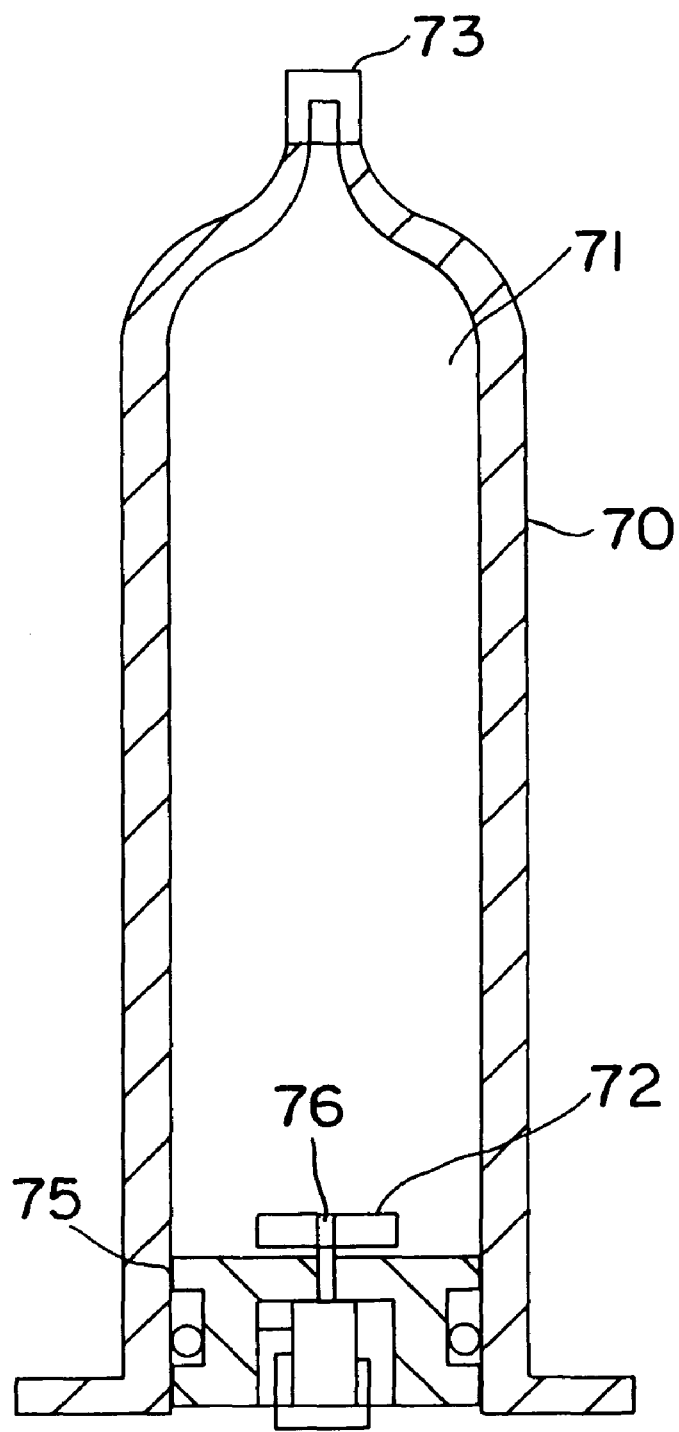
FIG. 11 is a schematical representation of an embodiment of the invention where hydrogen flows directly through the liquid and carries the liquid vapor into the gas phase.

FIG. 11 shows an embodiment of the invention where the hydrogen is dissipated continuously as it is produced. This embodiment can be utilized if the liquid is to be dispensed so that it can vaporize into the environment. Such liquids include some fragrances and insect repellants or insecticides. Liquid 71 is contained within syringe container 70. Hydrogen gas generator/activation clip assembly is sealed to fixture 75 which fits into the base of said liquid container 70. A hydrogen permeable film 72 such as OPP or PFA may be utilized to prevent the liquid from entering the gas inlet port 76. Micro-porous film covers the liquid vapor exit port 73. As hydrogen gas is generated, it passes directly through the liquid to be dispensed. The hydrogen becomes saturated with the liquid before it passes through said microporous film at the vapor exit port.

Figure 12:
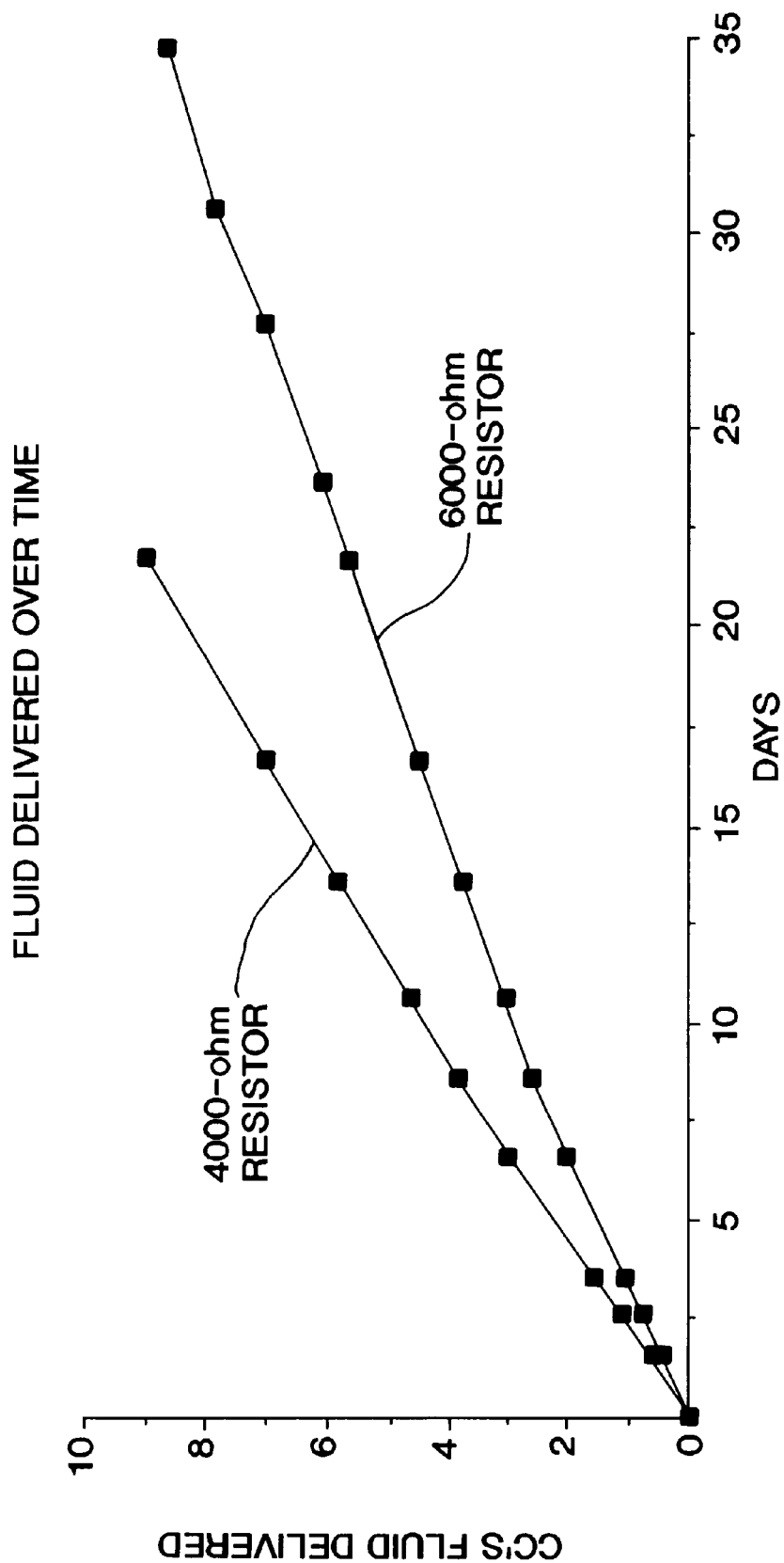
FIG. 12 shows a plot of liquid dispensed versus time with an electrochemical type gas generator, where the gas chamber and liquid chamber shells were constructed of Barex® film.

FIG. 12 shows a plot of volume liquid dispensed versus time utilizing a galvanic gas generating cell and reservoir similar to the embodiment of the invention shown in FIG. 2. The gas generation cells were constructed similar to zinc/air batteries in that they had an amalgamated zinc gel anode in an alkaline electrolyte. The cathode was a nickel expanded metal screen to which PTFE coated carbon was pressed. A porous fluoropolymer hydrophobic barrier 15b was pressed to the gas side of the cathode mesh 14 and a second porous fluoropolymer hydrophobic sealing layer 15a was placed between barrier 15b and a nonwoven polypropylene gas distribution mesh 16 which was placed between the cathode and the exit ports 6a of the can 9. An intermediate 0.001 inch thick Mylar® moisture barrier 17 covered the gas flow holes as shown in FIG. 4B and such that the gas permeated through the moisture barrier before entering the gas chamber. As the gas generated increased the pressure behind the intermediate moisture barrier 17, the moisture barrier flexed, increasing the effective permeation area as shown in FIG. 4C. The gas chamber 1 was constructed substantially of a PAN based material Barex® which was 0.0125 inches thick and had approximately 10 $cm^2$ area, the Barex® also had coating layers which facilitated forming a hermetic seal 23. The flexible diaphragm 3 was constructed of EVOH film of 0.003 inch thickness. A non aqueous fluid was dispensed which had a viscosity of about 1 centipoise. The gas generating cells where operated galvanically with either a 4000 ohm or 6000 ohm resistor 20 in the circuit between anode and cathode. Two curves are shown indicating the volumes of fluid delivered with respect to time over a period of several days.

Figure 13:
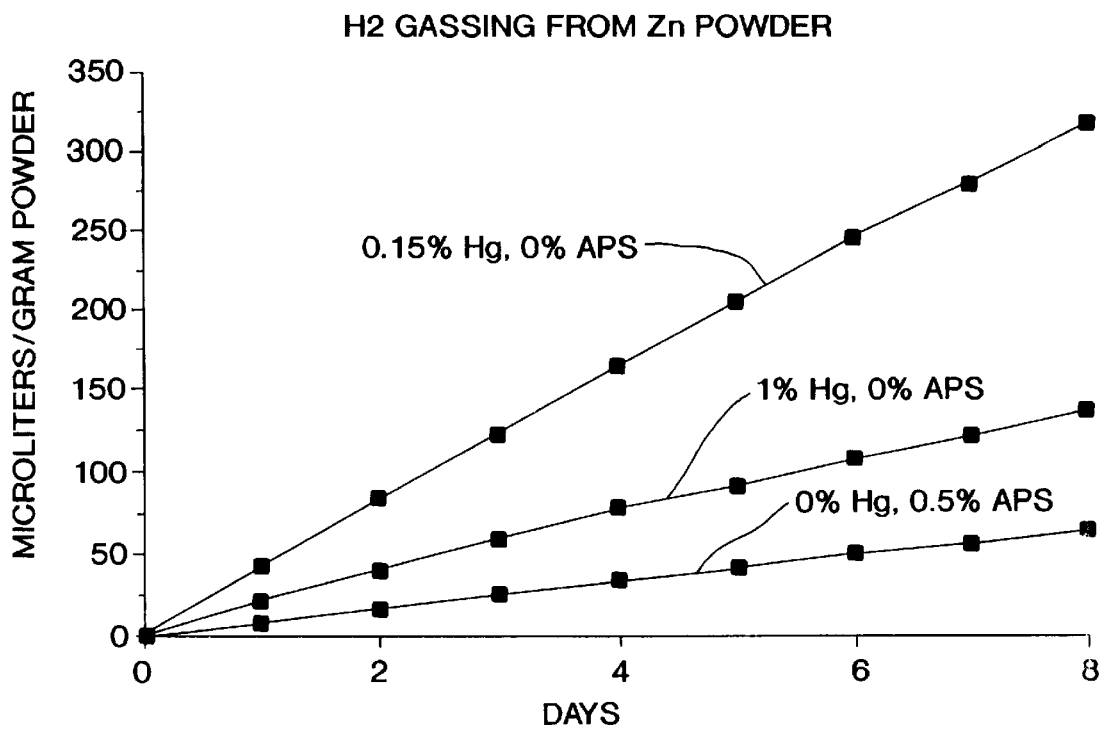
FIG. 13 shows a plot of gas generation versus time with a chemical type gas generator.

The data plotted in FIG. 13 is from Jacus's U.S. Pat. No. 5,034,291. Hydrogen gas evolves from a mixture of zinc containing 150 ppm indium and various amounts of additives when the zinc has been mixed with electrolyte consisting of 38 weight % potassium hydroxide, 3 weight % zinc oxide and water. The additives in this case were mercury and or aluminum potassium sulfate. The plot shows that rate of hydrogen generated is at a nearly constant rate, and that the rate is affected by the type and level of additives in the mix. These types of hydrogen generation curves are possible utilizing the embodiment of the invention as shown in FIGS. 6a&b. This embodiment is capable of very long shelf life.

Figure 14:
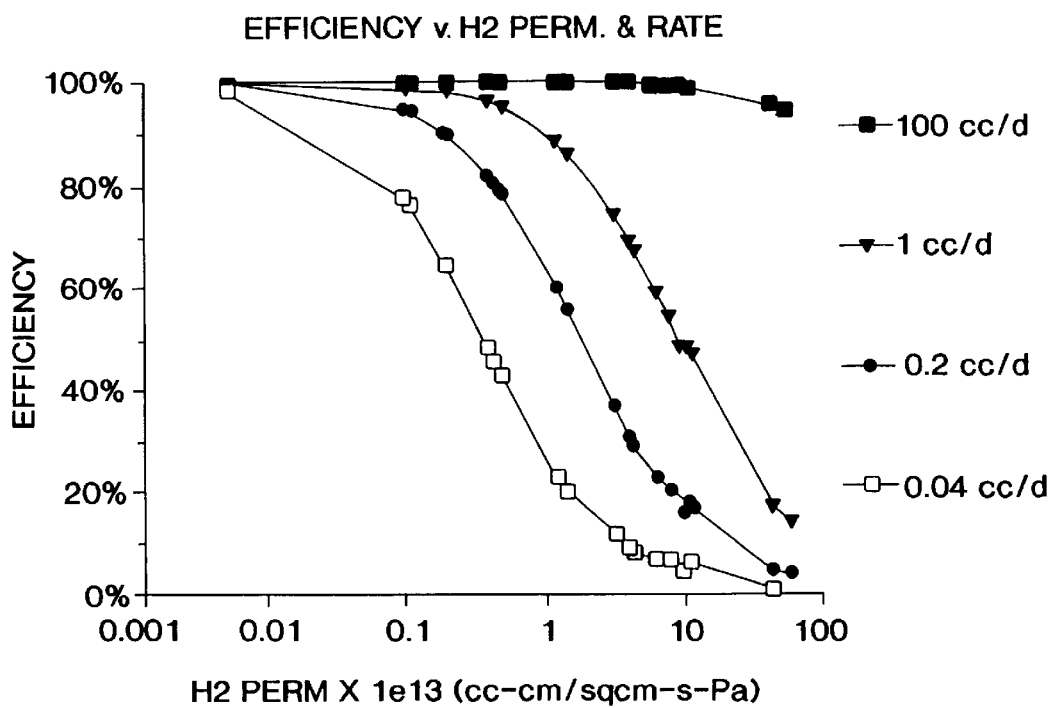
FIG. 14 shows a plot of efficiency versus hydrogen permeability coefficients at various rates.

FIG. 14 shows the ratio of liquid volume pumped versus the volume of hydrogen gas generated (or efficiency) for bladder systems composed of various monolayer materials where the area is held constant at 10 $cm^2$ and the material thickness is held constant at 0.015 inches. The plot is efficiency versus hydrogen permeation coefficient which has been multiplied by $10^{13}$, where the coefficient units are cc-cm/$cm^2$-s-Pa. Curves representing rates of 1, 0.2 and 0.04 cc's per day are shown. The efficiency is higher when the hydrogen permeability is lower, also as dispensing rates are lower, efficiency is lower because of the increased gas loss over time.

Figure 15:
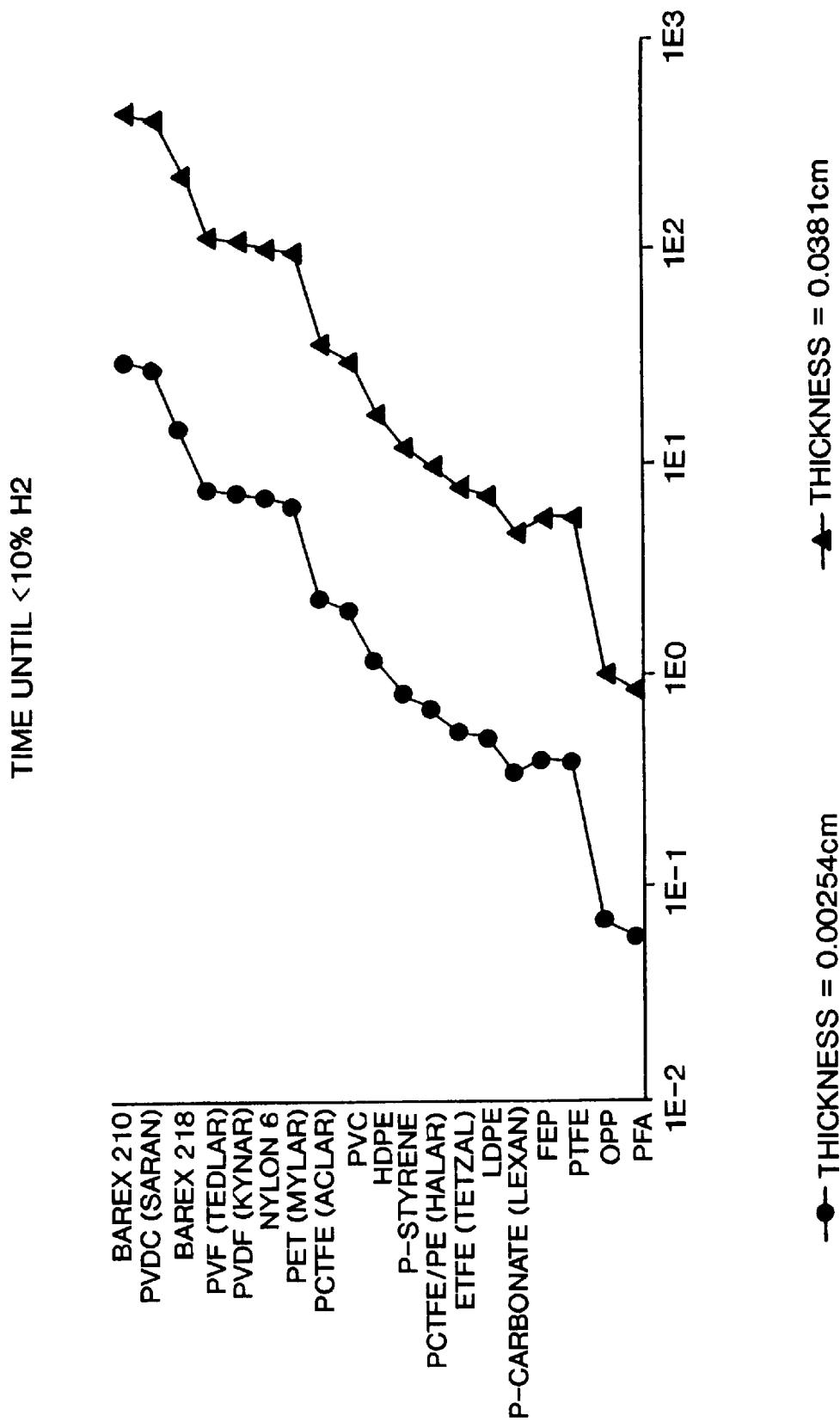
FIG. 15 shows a plot of the time it takes for the hydrogen concentration to dissipate to 10% versus shell construction material of two thicknesses.

FIG. 15 shows the time in days at 25° C. required for the hydrogen concentration inside a gas chamber bladder to drop to less than 10% once the device becomes inactive assuming that the starting concentration is 100% and that the gas chamber shell is constructed of various monolayer materials of either 0.00254 cm (0.001 inches) or 0.0381 cm (0.015 inches).

Figure 16:
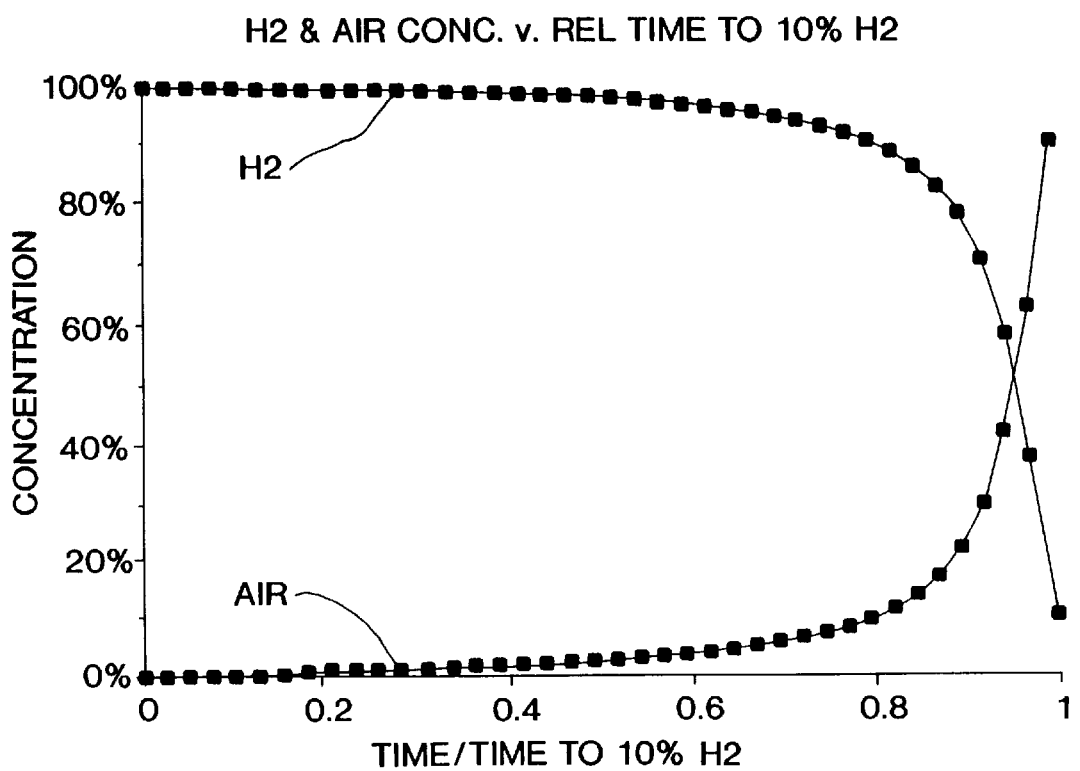
FIG. 16 shows the relative concentrations of hydrogen and air versus the relative time until the hydrogen concentration reaches 10%.

FIG. 16 shows the relative concentrations of hydrogen and air versus the relative time until the hydrogen concentration reaches 10%. This plot assumes that the shell is constructed of PET but the plot is very similar for other materials.

Figure 17A:
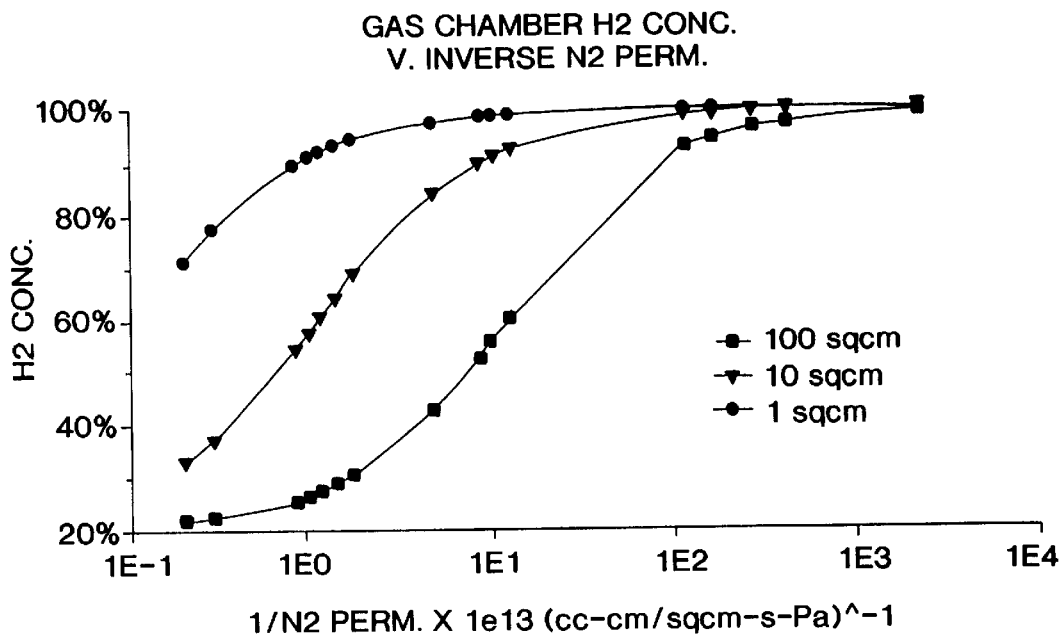
FIGS. 17a and 17b show a plots of hydrogen concentration versus inverse nitrogen permeability coefficient with varying areas and varying rates respectively.

FIG. 17a shows hydrogen concentration for bladder systems composed of various monolayer materials possessing various nitrogen permeation constants, and where the area is varied from 1–100 $cm^2$. The material thickness is held constant at 0.015 inches and the fluid delivery rate is held constant at 0.2 cc per day. The plot is hydrogen concentration versus inverse nitrogen permeation coefficient which has been multiplied by $10^{13}$, where the coefficient units are cc-cm/$cm^2$-s-Pa. Curves representing 1, 10 and 100 $cm^2$ area are shown.

Figure 17B:
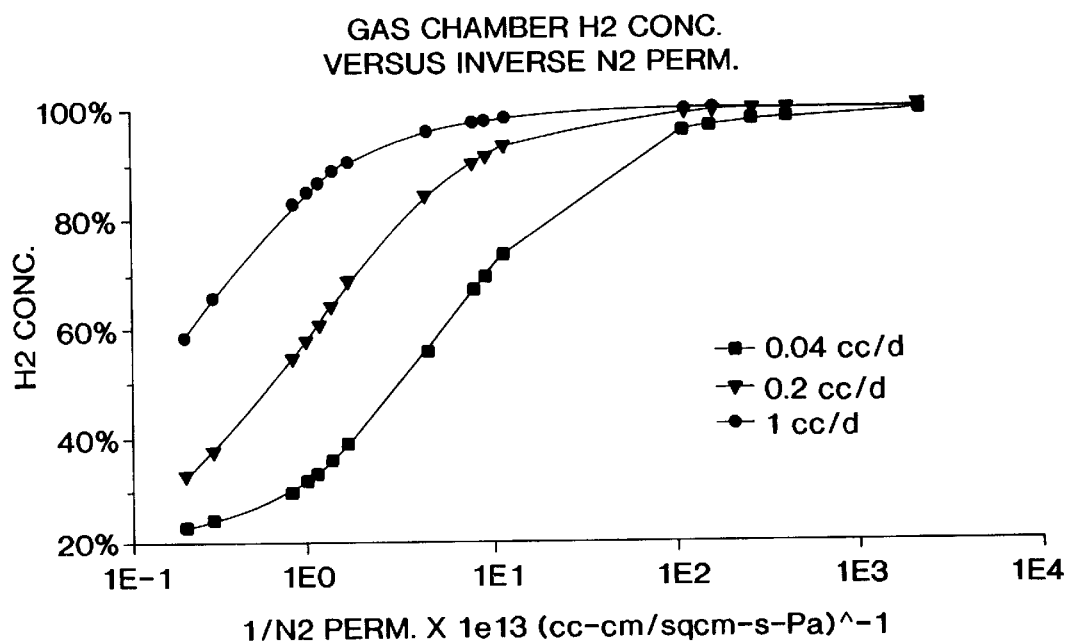

Similarly, FIG. 17b shows hydrogen concentration for bladder systems composed of various monolayer materials possessing various nitrogen permeation constants, and where the fluid delivery rate is varied. The material thickness is held constant at 0.015 inches and the area at 10 cm². The plot is hydrogen concentration versus inverse nitrogen permeation coefficient which has been multiplied by $10^{13}$, where the coefficient units are cc-cm/cm²-s-Pa. Curves representing 0.04, 0.2 and 1 cc per day fluid delivery rate are shown.

Figure 18:
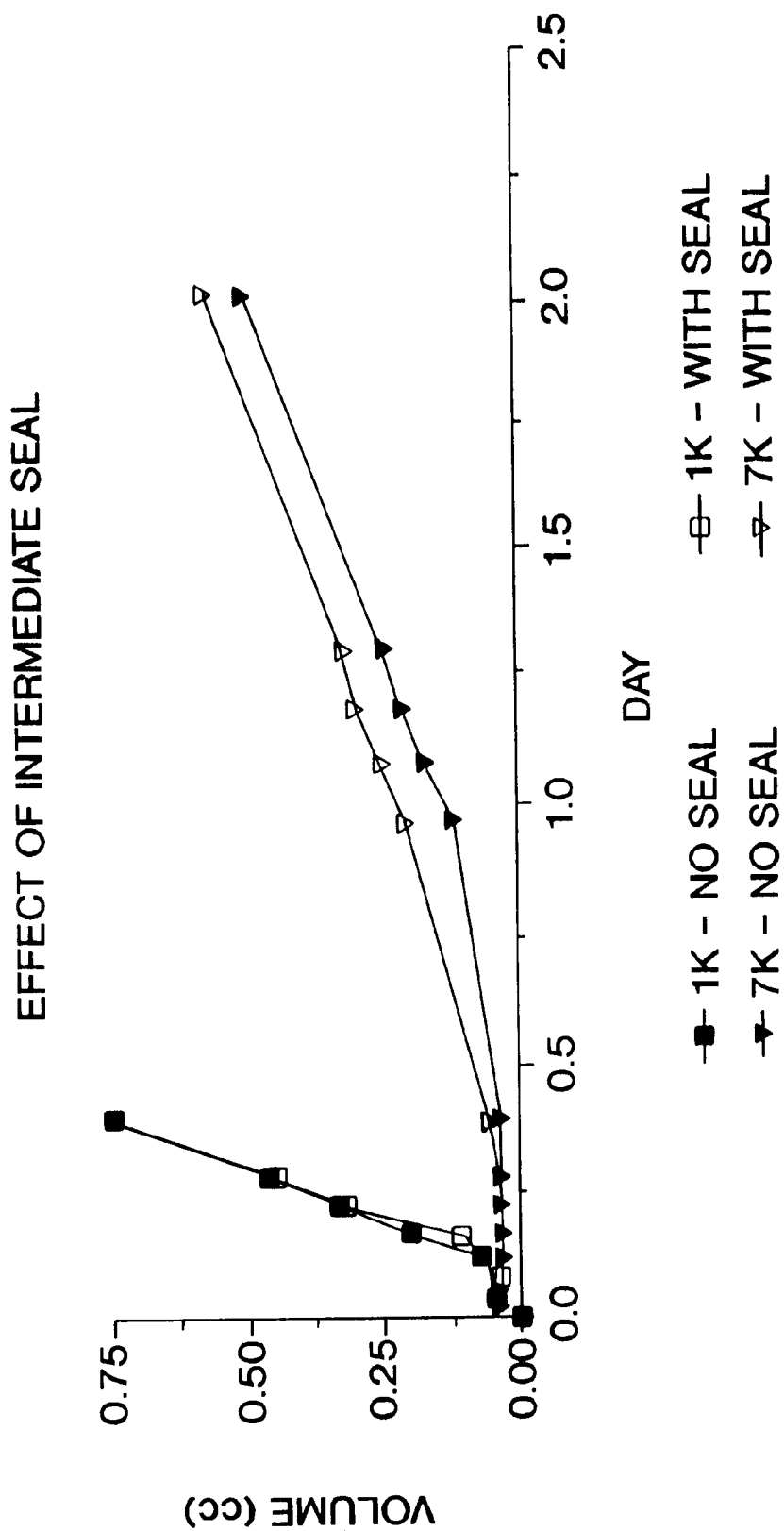
FIG. 18 shows the benefit of utilizing an intermediate moisture barrier between an electrochemical gas generating device and the gas chamber. The plot shows liquid volume dispensed of devices operated at different rates, with and without the intermediate moisture barrier.

FIG. 18 shows the benefit of utilizing an intermediate moisture barrier between an electrochemical gas generating device and the gas chamber. The plot shows liquid volume dispensed of devices operated at different rates, with and without the intermediate moisture barrier. The gas generation cells and gas chamber/liquid chamber reservoir construction and fluid dispensed were the same as described for FIG. 12.

Figure 19:
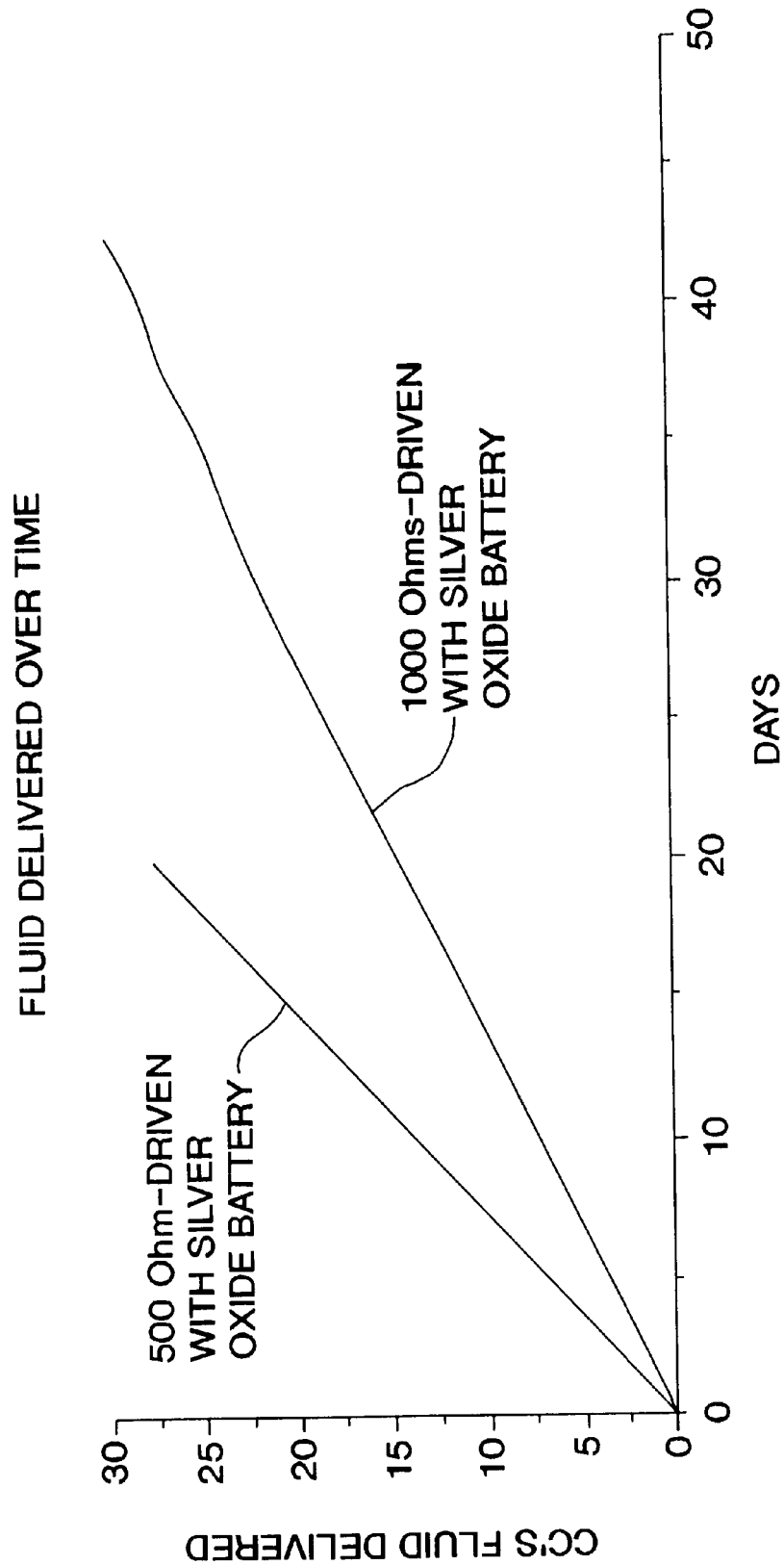
FIG. 19 shows a plot of fluid delivery volume versus time of a device as in FIG. 7. The plot shows the benefits of driving the gas delivery cell with a battery.

FIG. 19 shows a plot of fluid delivery volume versus time of a device as shown schematically in FIG. 7. The plot shows the benefits of driving the gas delivery cell with a battery.

EXAMPLE 1

A device was designed such that the gas generator was of the type disclosed in Winsel's U.S. Pat. No. 5,242,565. The gas generator was sized such that it was similar to a 675 zinc/air battery. The device needed to deliver 10 cc's of fluid at 1 atmosphere pressure. The gas chamber had 10 cm² area and could have a maximum thickness of 0.015 inches. Moisture loss through the flexible diaphragm and out through the liquid chamber shell was to be considered negligible due to low solubility in the liquid. The shelf-life requirement was 2 years in 100° F. at 20% relative humidity or 90% humidity. The alkaline electrolyte used in Winsel's gas generating cell would typically have an moisture equilibrium with environment at 60% relative humidity. That is, at humidities above 60%, the electrolyte would absorb moisture from the environment; at humidities below 60%, the electrolyte would lose moisture to the environment. Such an assumption is true for many electrolytes utilized in the battery industry. The design criteria called for 50% excess zinc than theoretical and to insure that the device would operate at a constant rate of 0.2 cc per day, the assumption is made that less than 20% volume change of the gas generating cell's constituents could be permitted. In the battery industry the assumption is typically made that less than 15% volume change can be permitted. Winsel provides in his gas generating cells, absorbent materials to provide moisture necessary to make-up the water consumed in the reaction:

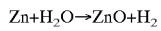

Also moisture carried into the gas chamber must be considered. However, Winsel neglects the overwhelming loss of moisture which may occur during storage or during the life of the pumping device which can far exceed any moisture consumed in reaction or transported to the gas chamber. Winsel also neglects the detrimental condition which would occur if an initially full gas generating cell absorbed appreciable moisture in a high humidity environment during storage or during the life of the product. The gas generating cell may leak electrolyte into the gas chamber and flood the porous portions of the gas generating cell where hydrogen is intend to flow away from the site of hydrogen evolution. Such a condition has a detrimental impact on gas generating cell performance. The volume available in the gas generating cell exclusive of the hydrogen evolving cathode in 675 battery hardware is approximately 0.330 cc. If PVDC is considered for the shell because of its low moisture permeability property, from FIG. 14 it can be determined that at 0.2 cc per day dispensing rate that the efficiency will be about 95%. Thus, the required zinc is 42.2 mg or 0.0059 cc leaving 0.324 cc for electrolyte assuming that the gas generating cell is completely filled. If the absorbing members recommend by Winsel are utilized, then only a fraction of 0.324 cc would be available for electrolyte. But assuming the larger amount of 0.324 cc, approximately 302 mg water would be contained. Of that 302 mg water, 7.7 mg water will be consumed in the gas generating cell reactions, and 0.1 mg water will be transported into the fully expanded gas chamber assuming that the gas chamber equilibrate with the gas generating cell electrolyte at standard temperature and pressure. To insure that the volume change of the gas generating cell is less than 20%, the moisture lost to the environment though the gas chamber shell or other pathways must be less than 68 mg. However, the moisture loss during two year storage at 100° F. and 20% relative humidity would be approximately 84 mg. If the shell were OPP, HDPE, or PTFE, then the loss would be about 100 mg. If the shell were PET then the loss would be approximately 320 mg. Only PCTFE based materials such as Halar® or Aclar® or metallized films would satisfy the criteria for 2 year shelf life. These materials may be prohibitively expensive for some applications.

EXAMPLE 2

Under the same design criteria as described in Example 1, an alternative which would increase the possibilities for gas chamber shell materials is to utilize an intermediate seal. If a moisture barrier is utilized as shown in FIGS. 4B or 4D and if the area of the gas outlet ports amount to 0.009 square centimeters and if the moisture barrier is 0.001 inch thick, then the moisture loss during the storage period under the conditions described above would be less than 5 mg for a large number of readily available materials including OPP, HDPE, LDPE, and PET, other materials which would limit moisture loss to less than 5 mg would include PFA, FEP, PTFE, PVDC, PCTFE or Aclar®, PCTFE/PE or Halar® or metallized films. These materials would also permit permeation of inadvertent hydrogen produced during storage. All of the materials would reduce start-up delay due to oxygen which may be in the headspace between in the gas chamber at the time of activation to varying degrees. If a film were utilized which was metallized with palladium, iron/titanium alloy, or nickel, there would be virtually no start-up delay. PET, PCTFE or Aclar® or PCTFE/PE or Halar® have low oxygen permeability but have high enough hydrogen permeability such that permanent intermediate moisture barriers could be utilized as shown in FIGS. 4B and 4C and also provide adequate barrier to moisture loss for the storage criteria.

EXAMPLE 3

Under the same design criteria as described in Example 1 a non permeable gas chamber shell could be utilized constructed from metal with a window covered with a material which would permit inadvertent hydrogen generated during storage but inhibit moisture permeation. If the window has area of 0.009 square inches, then the same materials suitable for the intermediate moisture barrier in Example 2 would be suitable for covering the window assuming 0.001 inch thickness.

EXAMPLE 4

Under the same design criteria as described in Example 1 an additional criteria is added where the gas chamber is to have a hydrogen concentration less than 10% within 10 days after the device stops generating hydrogen. From FIG. 15 one can determine that the materials PFA, OPP, PTFE, FEP, polycarbonate or Lexan®, LDPE, or LLDPE, ETFE, and PCTFE/PE or Halar® would be candidates to meet the criteria. Suppose LDPE or LLDPE are considered because they are readily available and Halar® is considered because of its low moisture permeability properties. The hydrogen permeability of typical commercial films of these materials is $7.4 \times 10^{-13}$ LDPE and LLDPE and $4.0 \times 10^{-13}$ cc-cm/sqcm-s-Pa for Halar®. From FIG. 14 it can be determined that with 10 square centimeters area and 0.015 inch thickness, the fluid delivery devices would operate at approximately 20% and 30% efficiency respectively. Since the moisture permeability of LDPE is high, an intermediate moisture barrier would be required to insure moisture retention during storage at low humidity or to prevent moisture gain in high humidities. A gas generator sized like the 675 battery is large enough to generate the extra hydrogen required to operate at either 20% or 30% if the volume to be delivered is 10 cc. Since more zinc must be utilized and more water consumed in the reaction, less water can be lost to the environment during storage. In the case of 20% efficiency, the maximum moisture loss would be 48 mg and in the case of 30% efficiency the maximum loss would be 56 mg. With PCTFE/PE or Halar® the moisture loss during 2 years at 100° F. and 20% humidity would be limited to 9 mg and thus be acceptable without an intermediate moisture barrier. Another acceptable candidate would be a combination of materials such as a 0.003 inch layer of Halar® and 0.012 inch layer of LDPE or LLDPE. The materials could be laminated or castrated. The layer of Halar® would provide adequate moisture barrier, limiting the moisture loss to 45 mg so that an intermediate moisture barrier would not be required and the final structure would meet the requirement that the gas chamber would be <10% hydrogen within 10 days after the device stops generating hydrogen.

These examples illustrate the importance of knowing the materials of construction since they dramatically affect both shelf-life, and ultimate operating efficiency which in turn affects the amount of active materials which must be included in the gas generator for a particular application.

What is claimed is:

1. A fluid delivery device comprising:

a chamber having a fluid and an opening;

a gas generating cell capable of directing gas into the chamber, to, in turn, direct fluid through the opening; and a gas permeable barrier positioned between the chamber and the gas generating cell, the gas permeable barrier having low moisture permeability.

2. The fluid delivery device according to claim 1 wherein the chamber is positioned so as to be one of substantially above and substantially below the gas generating cell.

3. The fluid delivery device according to claim 1 wherein the fluid comprises a fragrant fluid.

4. The fluid delivery device according to claim 1 wherein at least a portion of the fluid that exits from the opening in the chamber upon activation of the gas generating cell comprises a liquid.

5. The fluid delivery device according to claim 1 wherein at least a portion of the fluid that exits from the opening in the chamber upon activation of the gas generating cell comprises a vapor.

* * * * *